(12) United States Patent
Meerpoel et al.

(10) Patent No.: US 8,158,783 B2
(45) Date of Patent: *Apr. 17, 2012

(54) MTP INHIBITING TETRAHYDRO-NAPHTHALENE-1-CARBOXYLIC ACID DERIVATIVES

(75) Inventors: Lieven Meerpoel, Beerse (BE); Leo Jacobus Jozef Backx, Arendonk (BE); Peter Ten Holte, Beerse (BE); Guuske Frederike Busscher, Turnhout (BE)

(73) Assignee: Janssen Pharmaceutica N.V., Beerse (BE)

(*) Notice: Subject to any disclaimer, the term of this patent is extended or adjusted under 35 U.S.C. 154(b) by 206 days.

This patent is subject to a terminal disclaimer.

(21) Appl. No.: 12/446,581

(22) PCT Filed: Oct. 22, 2007

(86) PCT No.: PCT/EP2007/061289
§ 371 (c)(1), (2), (4) Date: Apr. 22, 2009

(87) PCT Pub. No.: WO2008/049808
PCT Pub. Date: May 2, 2008

(65) Prior Publication Data
US 2010/0016291 A1   Jan. 21, 2010

(30) Foreign Application Priority Data
Oct. 24, 2006 (EP) .................. 06122820

(51) Int. Cl.
*A61K 31/55* (2006.01)
*A61K 31/4439* (2006.01)
*A61K 31/165* (2006.01)
*A61K 31/5377* (2006.01)
*C07D 223/12* (2006.01)
*C07D 401/12* (2006.01)
*C07D 413/12* (2006.01)
*C07C 233/00* (2006.01)

(52) U.S. Cl. ............. 540/606; 546/279.1; 564/161; 544/124; 514/617; 514/217.11; 514/343; 514/237.2

(58) Field of Classification Search .......... None
See application file for complete search history.

(56) References Cited

U.S. PATENT DOCUMENTS

| 5,712,279 | A | 1/1998 | Biller et al. |
| 2003/0114442 | A1 | 6/2003 | Heckel et al. |
| 2009/0325980 | A1 | 12/2009 | Meerpoel et al. |

FOREIGN PATENT DOCUMENTS

| EP | 0643057 A | 3/1995 |
| WO | WO 96/40640 A1 | 12/1996 |
| WO | WO 98/23593 A1 | 6/1998 |
| WO | WO 00/32582 A1 | 6/2000 |
| WO | WO 01/47899 A1 | 7/2001 |
| WO | WO 01/92241 A1 | 12/2001 |
| WO | WO 02/42291 A1 | 5/2002 |
| WO | WO 2008/049806 A1 | 5/2008 |

OTHER PUBLICATIONS

Gentles et al. disclose in Journal of the Chemical Society, Perkin Transactions I: 1991, 1423-1431.*
Schafer et al. Drug Discovery Today 2008, 13 (21/22), 913-916.*
J. G. Cannon Chapter Nineteen in Burger's Medicinal Chemistry and Drug Discovery, Fifth Edition, vol. I: Principles and Practice, Wiley-Interscience 1995, pp. 783-802, 784.*
Li et al. in Bioorganic & Medicinal Chemistry Letters 16 (2006) 3039-30.*
Samaha et al. in Nature Clinical Practice (5)8, 497-505 (2008).*
International Search Report, International Application No. PCT/EP2007/061289, Date of Mailing of International Search Report, Oct. 24, 2006.
Wetterau et al, "Purification and characterization of microsomal triglyceride and cholesteryl ester transfer protein from bovine liver microsomes.", Chemistry and Physics of Lipids, 1985, vol. 38, pp. 205-222.
Hudson D., "Methodological Implications of Simultaneous Solid-Phase Peptide Synthesis. 1. Comparison of Different Coupling Procedures.", Journal of Organic Chemistry, 1988, vol. 53, pp. 617-624.
Wilson and Gisvold, "Metabolic Changes of Drugs and Related Organic Compounds." *Textbook of Medicinal and Pharmaceutical Chemistry*, 1977, pp. 70-75.

(Continued)

*Primary Examiner* — Timothy Thomas
*Assistant Examiner* — Dennis Heyer

(57) ABSTRACT

The present invention is concerned with novel tetrahydro-naphthalene-1-carboxylic acid derivatives having apoB secretion/MTP inhibiting activity and concomitant lipid lowering activity. The invention further relates to methods for preparing such compounds, pharmaceutical compositions comprising said compounds as well as the use of said compounds as a medicine for the treatment of atherosclerosis, pancreatitis, obesity, hypertriglyceridemia, hypercholesterolemia, hyperlipidemia, diabetes and type II diabetes. Formula (I).

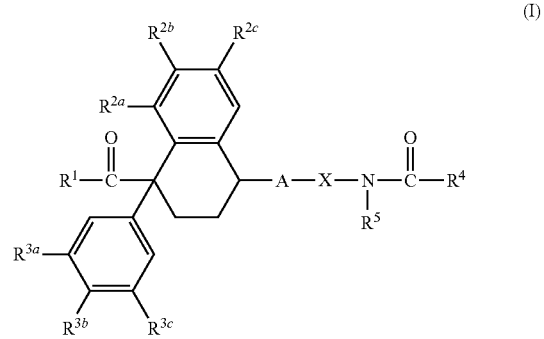

10 Claims, No Drawings

OTHER PUBLICATIONS

Dyatkin et al., "Determination of the Absolute Configuration of a Key Tricyclic Component of a Novel Vasopressin Receptor Antagonist by Use of Vibrational Circular Dichroism.", *Chirality*, 2002, vol. 14, pp. 215-219.

Albericio et al., "Coupling Methods: Solid Phase Formation of Amide and Ester Bonds.", Solid Phase Synthesis: A Practical Guide, Marcel Dekker, Inc., 2000 (ISBN: 0-8247-0359-6) pp. 275-330.

\* cited by examiner

MTP INHIBITING TETRAHYDRO-NAPHTHALENE-1-CARBOXYLIC ACID DERIVATIVES

CROSS REFERENCE TO RELATED APPLICATIONS

This application is the US national stage of Application No. PCT/EP2007/061289, filed Oct. 22, 2007, which application claims priority from EP 06122820.1 filed Oct. 24, 2006.

The present invention is concerned with novel tetrahydro-naphthalene-1-carboxylic acid derivatives having apoB secretion/MTP inhibiting activity and concomitant lipid lowering activity. The invention further relates to methods for preparing such compounds, pharmaceutical compositions comprising said compounds as well as the use of said compounds as a medicine for the treatment of atherosclerosis, pancreatitis, obesity, hypertriglyceridemia, hypercholesterolemia, hyperlipidemia, diabetes and type II diabetes.

Obesity is the cause of a myriad of serious health problems like the adult onset of diabetes and heart disease. In addition, losing weight is getting an obsession among an increasing proportion of the human population.

The causal relationship between hypercholesterolemia, particularly that associated with increased plasma concentrations of low density lipoproteins (hereinafter referred as LDL) and very low density lipoproteins (hereinafter referred as VLDL), and premature atherosclerosis and/or cardiovascular disease is now widely recognized. However, a limited number of drugs are presently available for the treatment of hyperlipidemia.

Drugs primarily used for the management of hyperlipidemia include bile acid sequestrant resins such as cholestyramine and colestipol, fibric acid derivatives such as bezafibrate, clofibrate, fenofibrate, ciprofibrate and gemfibrozil, nicotinic acid and cholesterol synthesis inhibitors such as HMG Co-enzyme-A reductase inhibitors. There still remains a need for new lipid lowering agents with improved efficiency and/or acting via other mechanisms than the above mentioned drugs.

Plasma lipoproteins are water-soluble complexes of high molecular weight formed from lipids (cholesterol, triglyceride, phospholipids) and apolipoproteins. Five major classes of lipoproteins that differ in the proportion of lipids and the type of apolipoprotein, all having their origin in the liver and/or the intestine, have been defined according to their density (as measured by ultracentrifugation). They include LDL, VLDL, intermediate density lipoproteins (hereinafter referred as IDL), high density lipoproteins (hereinafter referred as HDL) and chylomicrons. Ten major human plasma apolipoproteins have been identified. VLDL, which is secreted by the liver and contains apolipoprotein B (hereinafter referred as Apo-B), undergoes degradation to LDL which transports 60 to 70% of the total serum cholesterol. Apo-B is also the main protein component of LDL. Increased LDL-cholesterol in serum, due to oversynthesis or decreased metabolism, is causally related to atherosclerosis. In contrast high density lipoproteins (hereinafter referred as HDL), which contain apolipoprotein A1, have a protective effect and are inversely correlated with the risk of coronary heart disease. The HDL/LDL ratio is thus a convenient method of assessing the atherogenic potential of an individual's plasma lipid profile.

The two isoforms of apolipoprotein (apo) B, apo B-48 and apo B-100, are important proteins in human lipoprotein metabolism. Apo B-48, is about 48% the size of apo B-100 on sodium dodecyl sulfate-polyacrylamide gels, is synthesized by the intestine in humans. Apo B-48 is necessary for the assembly of chylomicrons and therefore has an obligatory role in the intestinal absorption of dietary fats. Apo B-100, which is produced in the liver in humans, is required for the synthesis and secretion of VLDL. LDL, which contain about ⅔ of the cholesterol in human plasma, are metabolic products of VLDL. Apo B-100 is virtually the only protein component of LDL. Elevated concentrations of apo B-100 and LDL cholesterol in plasma are recognized risk factors for developing atherosclerotic coronary artery disease.

A large number of genetic and acquired diseases can result in hyperlipidemia. They can be classified into primary and secondary hyperlipidemic states. The most common causes of the secondary hyperlipidemias are diabetes mellitus, alcohol abuse, drugs, hypothyroidism, chronic renal failure, nephrotic syndrome, cholestasis and bulimia. Primary hyperlipidemias have also been classified into common hypercholesterolaemia, familial combined hyperlipidaemia, familial hypercholesterolaemia, remnant hyperlipidaemia, chylomicronaemia syndrome and familial hypertriglyceridaemia.

Microsomal triglyceride transfer protein (hereinafter referred as MTP) is known to catalyze the transport of triglyceride, cholesteryl ester and phospholipids such as phosphatidylcholine. This indicates that MTP is required for the synthesis of Apo B-containing lipoproteins such as chylomicrons and VLDL, the precursor to LDL. It therefore follows that an MTP inhibitor would inhibit the synthesis of VLDL and LDL, thereby lowering levels of VLDL, LDL, cholesterol and triglyceride in humans. Compounds capable of inhibiting MTP are believed to be useful in the treatment of disorders such as obesity, hyperlipidemia, hypercholesterolemia, hypertriglyceridemia, class II diabetes, atherosclerosis and for the reduction of postprandial serum triglyceride plasma levels.

The present invention is based on the unexpected finding that a group of tetrahydro-naphthalene-1-carboxylic acid derivatives have apoB secretion/MTP inhibiting activity. These compounds of formula (I) can act systemically and/or as selective MTP inhibitors, i.e. is able to selectively block MTP at the level of the gut wall in mammals.

The present invention relates to a family of novel compounds of formula (I)

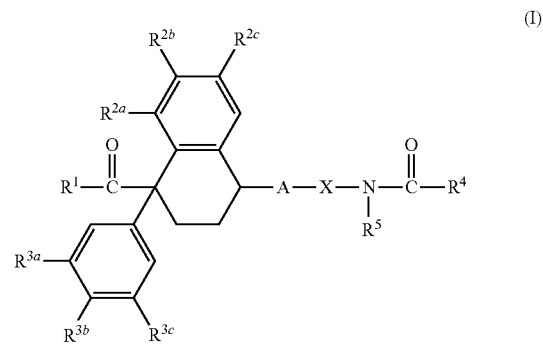

the pharmaceutically acceptable acid addition salts thereof, the N-oxides thereof, and the stereochemically isomeric forms thereof, wherein A is —$CH_2$— or —(C═O)—;

X represents

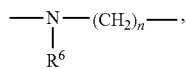 (a-1)

 (a-2)

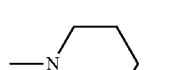 (a-3)

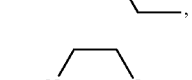 (a-4)

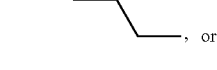 , or (a-4)

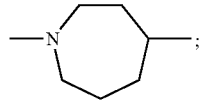 ; (a-5)

n is an integer 2 or 3;
$R^5$ is hydrogen or $C_{1-4}$alkyl;
$R^6$ is hydrogen or $C_{1-4}$alkyl;
$R^1$ is $NR^7R^8$, or $OR^9$;
  wherein each $R^7$ and $R^8$ are independently selected from
    hydrogen,
    $C_{1-8}$alkyl,
    $C_{1-8}$alkyl substituted with one, two or three substituents each independently from one another selected from halo, cyano, $C_{3-8}$cycloalkyl, $C_{1-4}$alkylcarbonyl, $C_{1-4}$alkyloxycarbonyl, polyhalo$C_{1-4}$alkyl, hydroxycarbonyl, —$OR^{10}$, —$NR^{10}R^{11}$, —$CONR^{12}R^{13}$, aryl, polycyclic aryl, of heteroaryl;
    $C_{3-8}$cycloalkyl;
    $C_{3-8}$cycloalkenyl;
    $C_{3-8}$alkenyl;
    $C_{3-8}$alkynyl;
    aryl;
    polycyclic aryl;
    heteroaryl;
    or $R^7$ and $R^8$ combined with the nitrogen atom bearing $R^7$ and $R^8$ may form an azetidinyl, pyrrolidinyl, piperidinyl, morpholinyl, azepanyl, or azocanyl ring wherein each of these rings may optionally be substituted by one or two substituents each independently selected from $C_{1-4}$alkyl, $C_{1-4}$alkyloxy, hydroxy, hydroxycarbonyl, or $C_{1-4}$alkyloxycarbonyl;
    wherein $R^{10}$ is hydrogen, $C_{1-4}$alkyl, $C_{1-4}$alkylcarbonyl, $C_{1-4}$alkyloxycarbonyl, aryl, polycyclic aryl, or heteroaryl;
    $R^{11}$ is hydrogen or $C_{1-4}$alkyl;
    $R^{12}$ is hydrogen, $C_{1-4}$alkyl or phenyl;
    $R^{13}$ is hydrogen, $C_{1-4}$alkyl or phenyl;
  $R^9$ is $C_{1-8}$alkyl,
    $C_{1-8}$alkyl substituted with one, two or three substituents each independently from one another selected from halo, cyano, $C_{3-8}$cycloalkyl, $C_{1-4}$alkylcarbonyl, $C_{1-4}$alkyloxycarbonyl, polyhalo$C_{1-4}$alkyl, hydroxycarbonyl, —$OR^{10}$, —$NR^{10}R^{11}$, —$CONR^{12}R^{13}$, aryl, polycyclic aryl, or heteroaryl;
    $C_{3-8}$cycloalkyl;
    $C_{3-8}$cycloalkenyl;
    $C_{3-8}$alkenyl;
    $C_{3-8}$alkynyl;
    aryl;
    polycyclic aryl;
    heteroaryl;
  wherein
    aryl is phenyl; phenyl substituted with one to five substituents each independently selected from $C_{1-4}$alkyl, $C_{1-4}$alkyloxy, halo, hydroxy, trifluoromethyl, cyano, $C_{1-4}$alkyloxycarbonyl, $C_{1-4}$alkyloxycarbonyl$C_{1-4}$alkyl, methylsulfonylamino, methylsulfonyl, $NR^{10}R^{11}$, $C_{1-4}$alkyl$NR^{10}R^{11}$, $CONR^{12}R^{13}$ or $C_{1-4}$alkyl$CONR^{12}R^{13}$;
    polycyclic aryl is naphthalenyl, indanyl, fluorenyl, or 1,2,3,4-tetrahydronaphtalenyl, and said polycyclic aryl is optionally substituted with one or two substituents each independently selected from $C_{1-6}$alkyl, $C_{1-6}$alkyloxy, phenyl, halo, cyano, $C_{1-4}$alkylcarbonyl, $C_{1-4}$alkyloxycarbonyl, $C_{1-4}$alkyloxycarbonyl$C_{1-4}$alkyl, $NR^{10}R^{11}$, $C_{1-4}$alkyl$NR^{11}R^{11}$, $CONR^{12}R^{13}$, $C_{1-4}$alkyl$CONR^{12}R^{13}$ or $C_{1-4}$alkyloxycarbonylamino and
    heteroaryl is pyridinyl, pyrazinyl, pyrimidinyl, pyridazinyl, triazinyl, triazolyl, imidazolyl, pyrazolyl, thiazolyl, isothiazolyl, oxazolyl, pyrrolyl, furanyl, thienyl; quinolinyl; isoquinolinyl; 1,2,3,4-tetrahydroisoquinolinyl; benzothiazolyl; benzo[1,3]dioxolyl; 2,3-dihydrobenzo[1,4]dioxinyl; indolyl; 2,3-dihydro-1H-indolyl; 1H-benzoimidazolyl; and said heteroaryl is optionally substituted with one or two substituents each independently selected from $C_{1-6}$alkyl, $C_{1-6}$alkyloxy, phenyl, halo, cyano, $C_{1-4}$alkylcarbonyl, $C_{1-4}$alkyloxycarbonyl, $C_{1-4}$alkyloxycarbonyl$C_{1-4}$alkyl, $NR^{10}R^{11}$, $C_{1-4}$alkyl$NR^{10}R^{11}$, $CONR^{12}R^{13}$ or $C_{1-4}$alkyl$CONR^{12}R^{13}$;
  $R^{2a}$, $R^{2b}$, and $R^{2c}$ are independently from one another selected from hydrogen, $C_{1-4}$alkyl, $C_{1-4}$-alkyloxy, halo, hydroxy, cyano, nitro, polyhalo$C_{1-4}$alkyl, polyhalo$C_{1-4}$alkyloxy or $C_{1-4}$alkyloxycarbonyl;
  $R^{3a}$, $R^{3b}$, and $R^{3c}$ are independently from one another selected from hydrogen, $C_{1-4}$alkyl, $C_{1-4}$alkyloxy, halo, hydroxy, cyano, nitro, polyhalo$C_{1-4}$alkyl, polyhalo$C_{1-4}$alkyloxy or $C_{1-4}$alkyloxycarbonyl;
  $R^4$ is phenyl; phenyl substituted with 1, 2, 3, or 5 substituents each independently selected from $C_{1-4}$alkyl, halo, hydroxy, $C_{1-4}$alkyloxy, cyano, nitro, polyhalo$C_{1-4}$alkyl, polyhalo$C_{1-4}$alkyloxy, $C_{1-4}$alkylcarbonyl, sulfamoyl, a heterocyclic group, or phenyl optionally substituted with 1, 2 or 3 substituents each independently selected from $C_{1-4}$alkyl, halo, $C_{1-4}$alkyloxy, or trifluoromethyl;
    or a heteroaryl selected from the group consisting of pyridinyl, pyrazinyl, pyrimidinyl, pyridazinyl, triazinyl, furanyl, and thienyl, wherein each of these heteroaryls may optionally be substituted with one or two substituents each independently selected from $C_{1-4}$alkyl, halo, hydroxy, $C_{1-4}$alkyloxy, oxo, cyano, polyhalo$C_{1-4}$-alkyl, $C_{1-4}$alkylcarbonyl, $C_{1-4}$alkyloxycarbonyl, or a heterocyclic group;
  wherein
  heterocyclic group is selected from azetidinyl, pyrrolidinyl, piperidinyl, piperazinyl, morpholinyl, azepanyl, and azocanyl which may optionally be substituted by one or two substituents each independently selected from $C_{1-4}$alkyl or halo.

As used in the foregoing definitions halo is generic to fluoro, chloro, bromo and iodo $C_{1-4}$alkyl defines straight and branched chain saturated hydrocarbon radicals having from 1 to 4 carbon atoms such as, for example, methyl, ethyl, propyl, butyl, 1-methyl-ethyl, 2-methylpropyl and the like $C_{1-6}$alkyl is meant to include $C_{1-4}$alkyl and the higher homologues thereof having 5 or 6 carbon atoms, such as, for example, 2-methylbutyl, pentyl, hexyl and the like;

$C_{1-8}$alkyl is meant to include $C_{1-6}$alkyl and the higher homologues thereof having 7 to 8 carbon atoms, such as for instance heptyl, ethylhexyl, octyl, and the like;

polyhalo$C_{1-4}$alkyl is defined as polyhalosubstituted $C_{1-4}$alkyl, in particular $C_{1-4}$alkyl (as hereinabove defined) substituted with 1 to 4 halogen atoms such as fluoromethyl, difluoromethyl, trifluoromethyl, trifluoroethyl, and the like;

$C_{3-8}$cycloalkyl is generic to cyclopropyl, cyclobutyl, cyclopentyl, cyclohexyl, cycloheptyl and cyclooctyl;

$C_{3-8}$cycloalkenyl is generic to cyclopropenyl, cyclobutenyl, cyclopentenyl, cyclohexenyl, cycloheptenyl and cyclooctenyl;

$C_{3-8}$alkenyl defines straight and branched chain hydrocarbon radicals containing one double bond and having from 3 to 8 carbon atoms such as, for example, 2-propenyl, 3-butenyl, 2-butenyl, 2-pentenyl, 3-pentenyl, 3-methyl-2-butenyl, 3-hexenyl, 2-hexenyl, 2-pentenyl, 2-octenyl and the like;

$C_{3-8}$alkynyl defines straight and branched chain hydrocarbon radicals containing one triple bond and having from 3 to 8 carbon atoms such as, for example, 2-propynyl, 3-butynyl, 2-butynyl, 2-pentynyl, 3-pentynyl, 3-methyl-2-butynyl, 3-hexynyl, 2-hexynyl, 2-pentynyl, 2-octynyl and the like.

The pharmaceutically acceptable acid addition salts as mentioned hereinabove are meant to comprise the therapeutically active non-toxic acid addition salt forms which the compounds of formula (I) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) may exist in both unsolvated and solvated forms. The term 'solvate' is used herein to describe a molecular complex comprising a compound of the invention and one or more pharmaceutically acceptable solvent molecules, e.g. ethanol. The term 'hydrate' is used when said solvent is water.

The N-oxide form of the compound according to formula (I) is meant to comprise a compound of formula (I) wherein one or several nitrogen atoms are oxidized to so-called N-oxides, particularly those N-oxides wherein one or more tertiary nitrogens (e.g. of the piperazinyl or piperidinyl radical) are N-oxidized. Such N-oxides can easily be obtained by a skilled person without any inventive skills and they are obvious alternatives for a compound according to formula (I) since these compounds are metabolites, which are formed by oxidation in the human body upon uptake. As is generally known, oxidation is normally the first step involved in drug metabolism (Textbook of Organic Medicinal and Pharmaceutical Chemistry, 1977, pages 70-75). As is also generally known, the metabolite form of a compound can also be administered to a human instead of the compound per se, with much the same effects.

A compound of formula (I) may be converted to the corresponding N-oxide form following art-known procedures for converting a trivalent nitrogen into its N-oxide form. Said N-oxidation reaction may generally be carried out by reacting the compound of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydro-carbons, e.g. dichloromethane, and mixtures of such solvents.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of formula (I) are obviously intended to be embraced within the scope of this invention.

The absolute stereochemical configuration of the compounds of formula (I) and of the intermediates used in their preparation may easily be determined by those skilled in the art while using well-known methods such as, for example, X-ray diffraction.

The compounds of formula (I) have at least two asymmetric carbon atoms as illustrated below wherein the asymmetric carbon atoms are identified by a *.

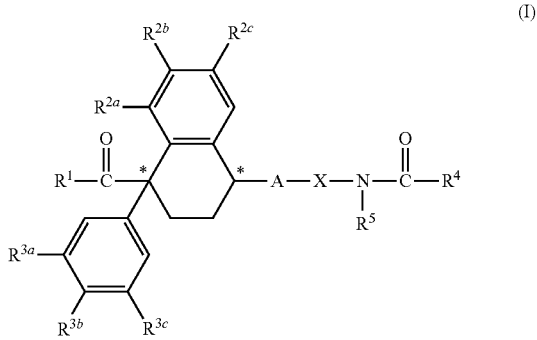

Due to the presence of at least two asymmetric carbon atoms, generally the term "a compound of formula (I)"

encompasses a mixture of four stereoisomers. Most compounds of the present invention have been prepared either with the trans-configuration or the cis-configuration:

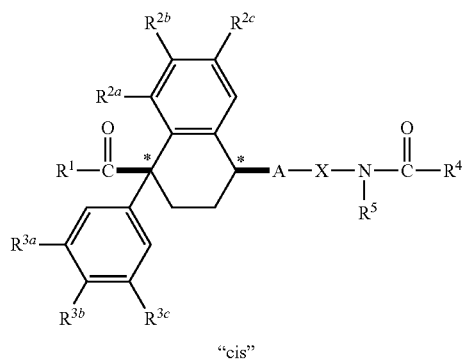

"cis"

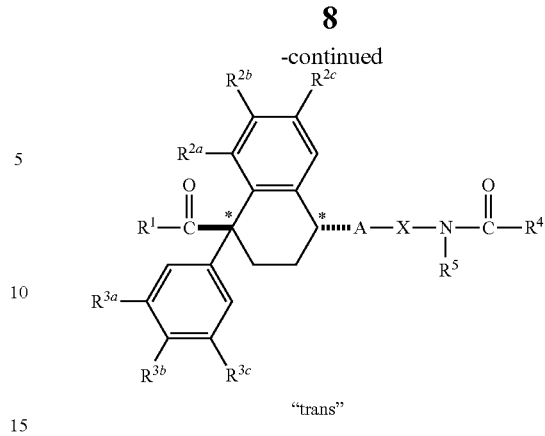

"trans"

Each of the above depicted "cis"- or "trans" compounds consists of a racemic mixture of two enantiomers and bold bonds or hashed bonds have been used to indicate this relative stereochemical configuration.

In case a "cis"- or "trans"-compound was separated into its two individual enantiomers, the bold and hashed bonds were replaced by wedged bonds to indicate the compound is a single enantiomer. If the absolute stereochemistry of a specific chiral carbon atom in a single enantiomer was not known, its stereochemical configuration was than designated as R*, or S* indicating a relative stereochemistry.

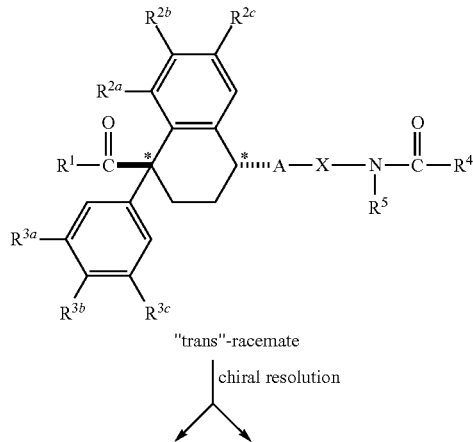

"trans"-racemate chiral resolution

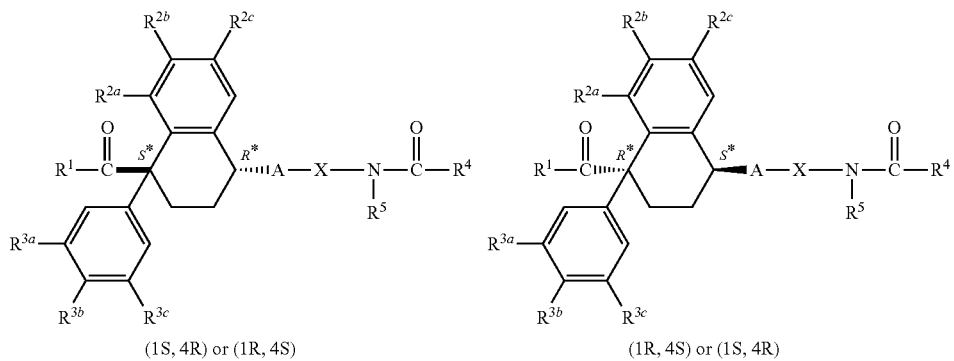

(1S, 4R) or (1R, 4S)　　　(1R, 4S) or (1S, 4R)

Furthermore, some compounds of formula (I) and some of the intermediates used in their preparation may exhibit polymorphism. It is to be understood that the present invention encompasses any polymorphic forms possessing properties useful in the treatment of the conditions noted hereinabove.

Some of the compounds of formula (I) may also exist in their tautomeric form. Such forms although not explicitly indicated in the above formula are intended to be included within the scope of the present invention. For instance, when an aromatic heterocyclic ring is substituted with hydroxy the keto-form may be the mainly populated tautomer.

In the framework of this application, with the expression "a compound according to the invention" it is also meant to include a compound according to the general formula (I) and a pro-drug thereof, or a isotopically labelled compound thereof.

Also within the scope of the invention are so-called "pro-drugs" of the compounds of formula (I). Pro-drugs are certain derivatives of pharmaceutically active compounds which may have little or no pharmacological activity themselves which can, when administered into or onto the body, be converted into compounds of formula (I) having the desired pharmaceutical activity, e.g. by hydrolytic cleavage. Such derivatives are referred to as "pro-drugs".

In the framework of this application, a compound according to the invention is inherently intended to comprise all isotopic combinations of its chemical elements. In the framework of this application, a chemical element, in particular when mentioned in relation to a compound according to formula (I), comprises all isotopes and isotopic mixtures of this element, either naturally occurring or synthetically produced, either with natural abundance or in an isotopically enriched form. In particular, when hydrogen is mentioned, it is understood to refer to $^1H$, $^2H$, $^3H$ and mixtures thereof; when carbon is mentioned, it is understood to refer to $^{11}C$, $^{12}C$, $^{13}C$, $^{14}C$ and mixtures thereof; when nitrogen is mentioned, it is understood to refer to $^{13}N$, $^{14}N$, $^{15}N$ and mixtures thereof; when oxygen is mentioned, it is understood to refer to $^{14}O$, $^{15}O$, $^{16}O$, $^{17}O$, $^{18}O$ and mixtures thereof; and when fluor is mentioned, it is understood to refer to $^{18}F$, $^{19}F$ and mixtures thereof.

A compound according to the invention therefore inherently comprises a compound with one or more isotopes of one or more element, and mixtures thereof, including a radioactive compound, also called radiolabelled compound, wherein one or more non-radioactive atoms has been replaced by one of its radioactive isotopes. By the term "radiolabelled compound" is meant any compound according to formula (I), a pharmaceutically acceptable acid or base addition salt thereof, an N-oxide form thereof, or a quaternary ammonium salt thereof, which contains at least one radioactive atom. For example, a compound can be labelled with positron or with gamma emitting radioactive isotopes. For radioligand-binding techniques (membrane receptor assay), the $^3H$-atom or the $^{125}I$-atom is the atom of choice to be replaced. For imaging, the most commonly used positron emitting (PET) radioactive isotopes are $^{11}C$, $^{18}F$, $^{15}O$ and $^{13}N$, all of which are accelerator produced and have half-lives of 20, 100, 2 and 10 minutes respectively. Since the half-lives of these radioactive isotopes are so short, it is only feasible to use them at institutions which have an accelerator on site for their production, thus limiting their use. The most widely used of these are $^{18}F$, $^{99m}Tc$, $^{201}Tl$ and $^{123}I$. The handling of these radioactive isotopes, their production, isolation and incorporation in a molecule are known to the skilled person.

In particular, the radioactive atom is selected from the group of hydrogen, carbon, nitrogen, sulfur, oxygen and halogen. Preferably, the radioactive atom is selected from the group of hydrogen, carbon and halogen.

In particular, the radioactive isotope is selected from the group of $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^3H$, $^{11}C$ and $^{18}F$.

In an embodiment, the present invention relates to those compounds of formula (I) wherein A represents —(C=O)—; $R^1$ is $OR^9$ wherein $R^9$ is $C_{1-6}$alkyl or $C_{3-8}$alkenyl; $R^{2a}$ $R^{3a}$, $R^{2b}$, $R^{3b}$, $R^{2c}$, and $R^{3c}$ are hydrogen; $R^4$ represents phenyl, phenyl substituted with $C_{1-14}$alkyloxy, phenyl substituted with halo, pyridinyl substituted with hydroxy, or pyridinyl substituted with $C_{1-4}$alkyloxy; and X represents radical (a-1) wherein $R^5$ is hydrogen and $R^6$ is hydrogen or $C_{1-4}$alkyl.

Interesting compounds of formula (I) are those compounds of formula (I) wherein one or more of the following restrictions apply:

a) X represents radical (a-1) wherein n is 2; or
b) X represents radical (a-1) wherein n is 3; or
c) X represents radical (a-2); or
d) X represents radical (a-4); or
e) X represents radical (a-5); or
f) $R^{2a}$=$R^{3a}$, $R^{2b}$=$R^{3b}$ and $R^{2c}$=$R^{3c}$; in particular $R^{2a}$=$R^{3a}$=H, $R^{2b}$=$R^{3b}$=H, and $R^{2c}$=$R^{3c}$=H, or
g) A is —(C=O)—; or
h) A is —CH$_1$—; or
i) $R^1$ is $NR^7R^8$ wherein each $R^7$ and $R^8$ are independently selected from hydrogen; $C_{1-8}$alkyl; $C_{1-8}$alkyl substituted with one, or two substituents each independently from one another selected from hydroxy, $C_{1-4}$-alkyloxy, $C_{1-4}$alkyloxycarbonyl, hydroxycarbonyl, $NR^{10}R^{11}$, $CONR^{12}R^{13}$, aryl, or heteroaryl; or aryl; or
j) $R^1$ is $NR^7R^8$ wherein $R^7$ and $R^8$ are combined with the nitrogen atom bearing $R^7$ and $R^8$ to form a pyrrolidinyl or piperidinyl ring wherein each of these rings may optionally be substituted by one or two substituents each independently selected from $C_{1-4}$alkyl, $C_{1-4}$alkyloxy, hydroxy, hydroxycarbonyl, or $C_{1-4}$alkyloxycarbonyl; or
k) $R^1$ is $OR^9$ wherein $R^9$ is $C_{1-8}$alkyl or $C_{3-8}$alkenyl; or
l) $R^4$ is phenyl; phenyl substituted with 1, 2 or 3 substituents each independently selected from $C_{1-4}$alkyl, halo, hydroxy, $C_{1-4}$alkyloxy, or polyhalo$C_{1-4}$alkyloxy; or heteroaryl selected from pyridinyl or pyridazinyl each optionally substituted with hydroxy or $C_{1-4}$alkyloxy.

In general compounds of formula (I) can be prepared by N-alkylating an intermediate of formula (II) with a carboxylic acid intermediate of formula (III), in at least one reaction-inert solvent and optionally in the presence of at least one suitable coupling reagent and/or a suitable base, the said process further optionally comprising converting a compound of formula (I) into an addition salt thereof, and/or preparing stereochemically isomeric forms thereof.

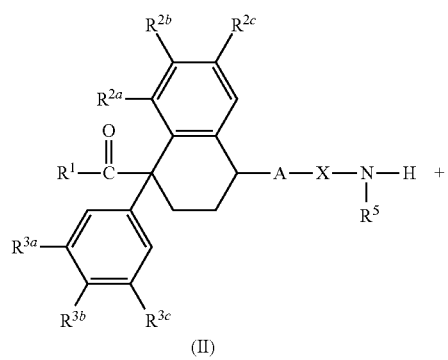

(II)

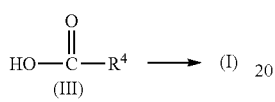

It may be convenient to activate the carboxylic acid of formula (III) by adding an effective amount of a reaction promoter. Non-limiting examples of such reaction promoters include carbonyldiimidazole, diimides such as N,N'-dicyclohexyl-carbodiimide or 1-(3-dimethylaminopropyl)-3-ethyl-carbodiimide, and functional derivatives thereof. The reaction may be performed in the further presence of an effective amount of a compound such as hydroxybenzotriazole (HOBT), benzotriazolyloxytris(dimethylamino)-phosphonium hexafluorophosphate, tetrapyrrolidinophosphonium hexafluorophosphate, bromotripyrrolidinophosphonium hexafluorophosphate, or a functional derivative thereof.

Compounds of formula (I-a), defined as compounds of formula (I) wherein radical A represents —(C=O)—, can be prepared by reacting an intermediate of formula (V) with an intermediate of formula (IV), in at least one reaction-inert solvent and optionally in the presence of at least one suitable coupling reagent and/or a suitable base, the said process further optionally comprising converting a compound of formula (I) into an addition salt thereof, and/or preparing stereochemically isomeric forms thereof.

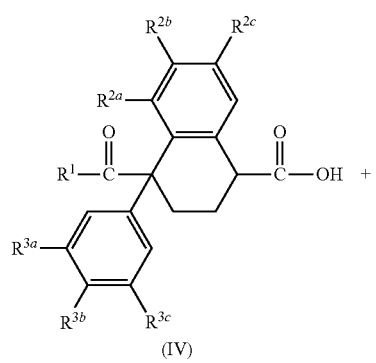

(IV)

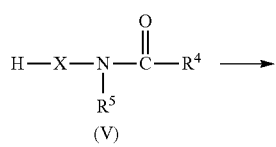

(V)

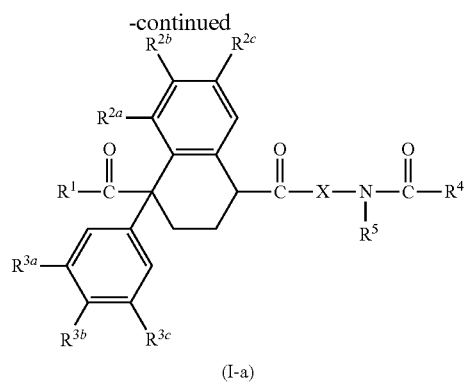

(I-a)

It may be convenient to activate the carboxylic acid of formula (IV) by adding an effective amount of a reaction promoter. Non-limiting examples of such reaction promoters include carbonyldiimidazole, diimides such as N,N'-dicyclohexyl-carbodiimide or 1-(3-dimethylaminopropyl)-3-ethyl-carbodiimide, and functional derivatives thereof. In case a chirally pure reactant of formula (IV) is used, a fast and enantiomerization-free reaction of the intermediate of formula (IV) with the said intermediate (V) may be performed in the further presence of an effective amount of a compound such as hydroxybenzotriazole (HOBT), benzotriazolyloxytris (dimethylamino)-phosphonium hexafluorophosphate, tetrapyrrolidinophosphonium hexafluorophosphate, bromotripyrrolidinophosphonium hexafluorophosphate, or a functional derivative thereof, such as disclosed by D. Hudson, it Org. Chem. (1988), 53:617.

Compounds of formula (I-b), defined as compounds of formula (I) wherein radical A represents —CH$_2$—, can be prepared by N-alkylating an intermediate of formula (V) with an intermediate of formula (IV-b) wherein W is an appropriate leaving group such as, for example, halo, e.g. chloro, bromo, iodo, or in some instances W may also be a sulfonyloxy group, e.g. methanesulfonyloxy, benzenesulfonyloxy, trifluoromethanesulfonyloxy and the like reactive leaving groups. The reaction can be performed in a reaction-inert solvent such as, for example, acetonitrile, 2-pentanol, isobutanol, dimethyl acetamide or DMF, and optionally in the presence of a suitable base such as, for example, sodium carbonate, potassium carbonate, or triethylamine. Stirring may enhance the rate of the reaction. The reaction may conveniently be carried out at a temperature ranging between room temperature and the reflux temperature of the reaction mixture.

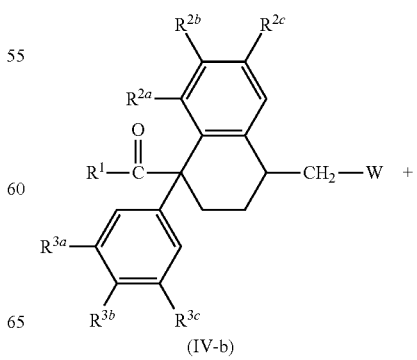

(IV-b)

-continued

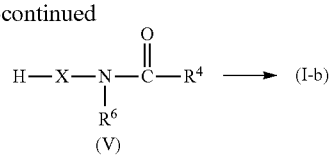

Intermediates of formula (II) can be prepared by reacting an intermediate of formula (IV) or an intermediate of formula (IV-b) with an intermediate of formula (VI), wherein PG is a protective group such as e.g. tert-butyloxycarbonyl or benzyl, with a carboxylic acid intermediate of formula (IV) in at least one reaction-inert solvent and optionally in the presence of at least one suitable coupling reagent and/or a suitable base; followed by removal of the protecting group PG.

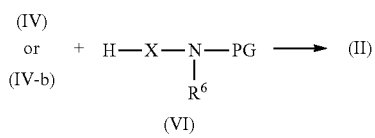

Intermediates of formula (V) can be prepared by reacting an intermediate of formula (VII), wherein PG is a protective group such as e.g. tert-butyloxycarbonyl or benzyl, with a carboxylic acid intermediate of formula (III) in at least one reaction-inert solvent and optionally in the presence of at least one suitable coupling reagent and/or a suitable base; followed by removal of the protecting group PG.

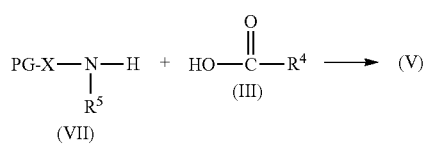

Intermediates of formula (XIII), defined as intermediates of formula (IV) wherein $R^1$ represents $OR^9$, $R^{2a}=R^{3a}$, $R^{2b}=R^{3b}$ and $R^{2c}=R^{3c}$, can be prepared as outlined below.

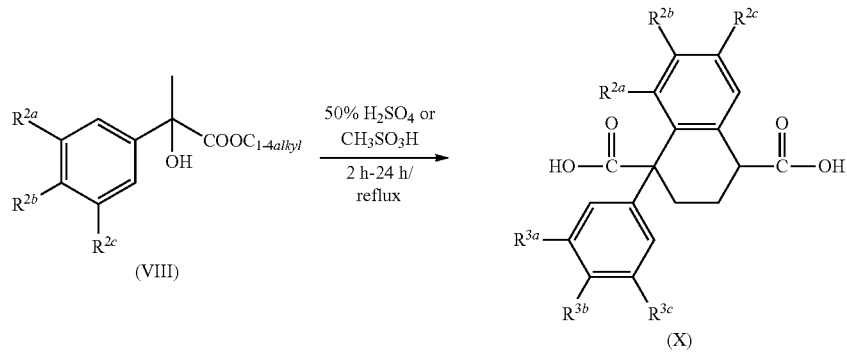

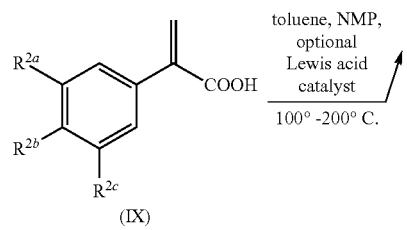

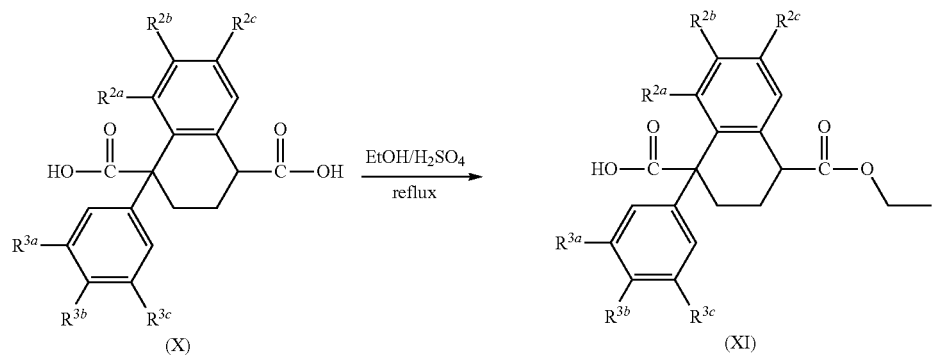

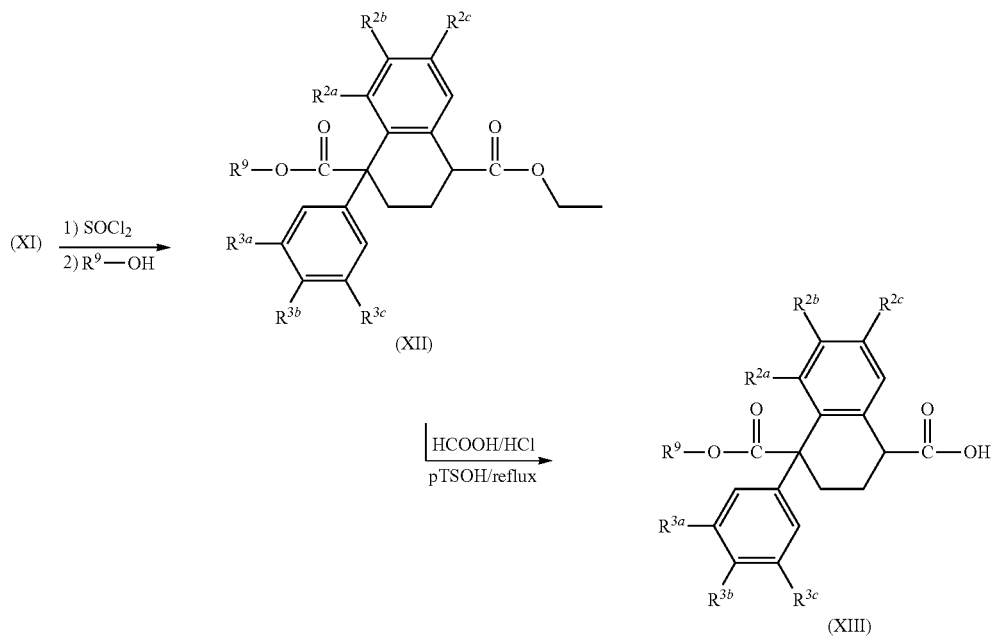

Intermediates of formula (XV) can be prepared as outlined below. The intermediates of formula (XV) are intermediates of formula (IV) wherein $R^1$ represents $NR^7R^8$.

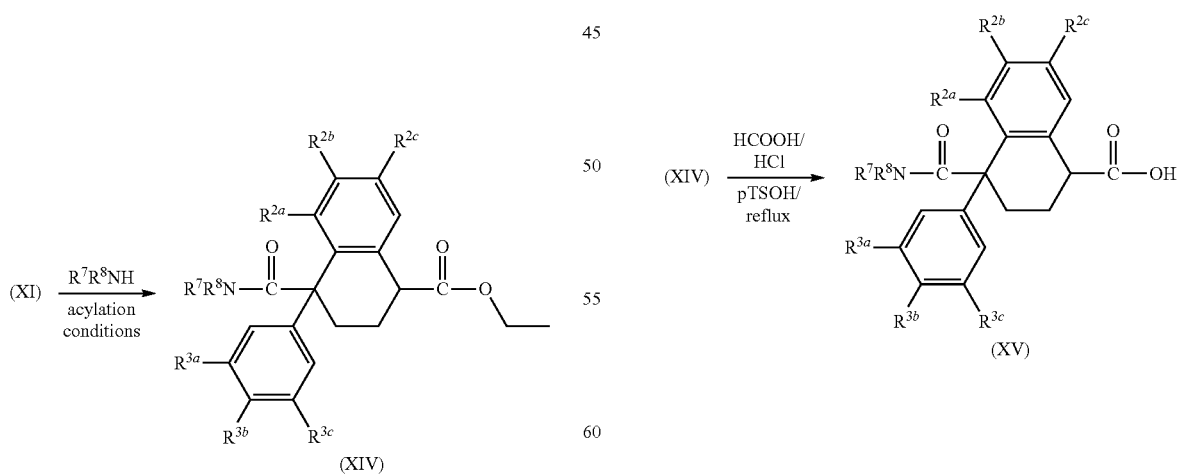

Intermediates of formula (IV-b) can be prepared as outlined below. Intermediates of formula (IV-b-1) are defined as intermediates of formula (IV-b) wherein $R^1$ represents $NR^7R^8$ and intermediates of formula (IV-b-2) are defined as intermediates of formula (IV-b) wherein $R^1$ represents $OR^9$.

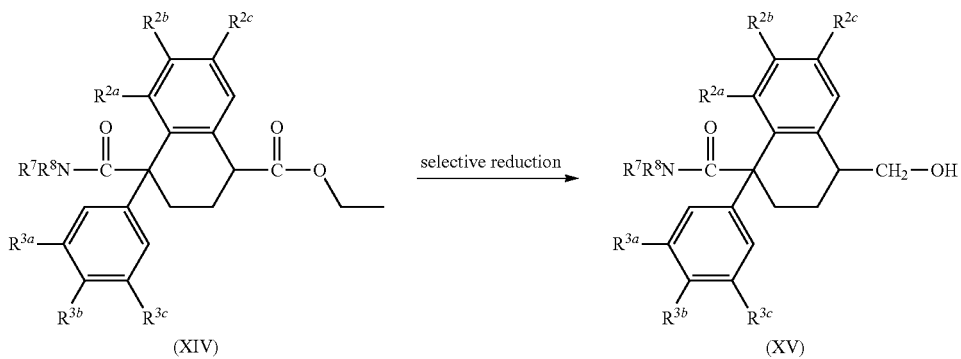
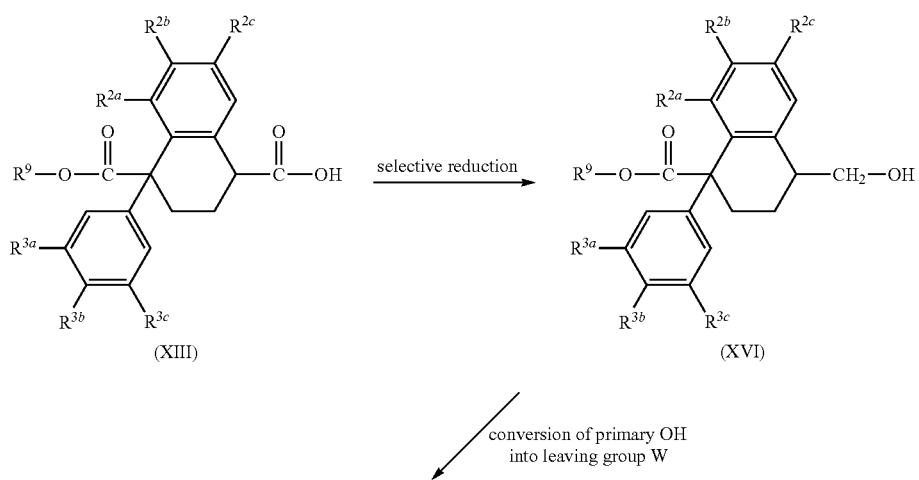
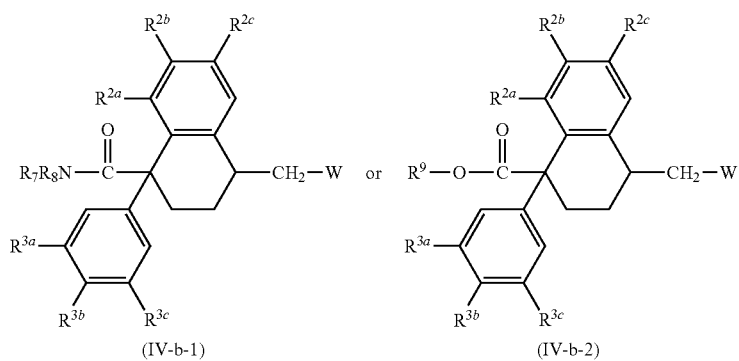

Intermediates of formula (XVII), wherein the substituents $R^{2a}$, $R^{2b}$, $R^{2c}$, $R^{3a}$, $R^{3b}$, $R^{3c}$, $R^4$, $R^5$, $A^1$, $A^2$, and X are as defined for compounds of formula (I), can be converted into compounds of formula (I-c), defined as compounds of formula (I) wherein $R^1$ represents $NR^7R^8$, by art-known N-acylation methods using $H-NR^7R^8$ as the reagent.

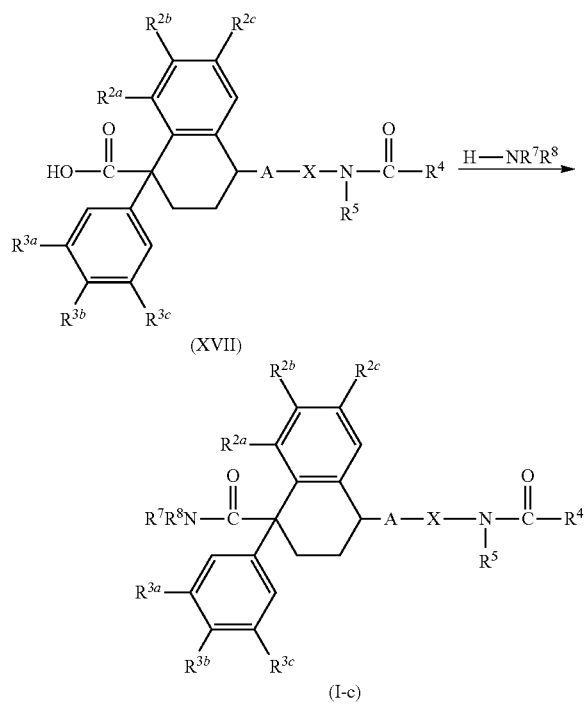

The compounds of formula (I) as prepared in the hereinabove described processes may be synthesized in the form of racemic mixtures of enantiomers which can be separated from one another following art-known resolution procedures. Those compounds of formula (I) that are obtained in racemic form may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I), the N-oxide forms, the pharmaceutically acceptable salts and stereoisomeric forms thereof possess favourable apoB secretion and MTP inhibiting activity and concomitant lipid lowering activity. Therefore the present compounds of formula (I) are useful as a medicine especially in a method of treating patients suffering from hyperlipidemia, obesity, atherosclerosis or type II diabetes. Subsequently the present compounds may be used for the manufacture of a medicine for treating disorders caused by an excess of very low density lipoproteins (VLDL) or low density lipoproteins (LDL), and especially disorders caused by the cholesterol associated with said VLDL and LDL. In particular the present compounds may be used for the manufacture of a medicament for the treatment of hyperlipidemia, obesity, atherosclerosis or type II diabetes.

The principal mechanism of action of the compounds of formula (I) appears to involve inhibition of MTP (microsomial triglyceride transfer protein) activity in hepatocytes and intestinal epithelial cells, resulting in decreased VLDL and chylomicron production, respectively. This is a novel and innovative approach to hyperlipidemia, and is expected to lower LDL-cholesterol and triglycerides through reduced hepatic production of VLDL and intestinal production of chylomicrons.

A large number of genetic and acquired diseases can result in hyperlipidemia. They can be classified into primary and secondary hyperlipidemic states. The most common causes of the secondary hyperlipidemias are diabetes mellitus, alcohol abuse, drugs, hypothyroidism, chronic renal failure, nephrotic syndrome, cholestasis and bulimia. Primary hyperlipidemias are common hypercholesterolaemia, familial combined hyperlipidaemia, familial hypercholesterolaemia, remnant hyperlipidaemia, chylomicronaemia syndrome, familial hypertriglyceridaemia. The present compounds may also be used to prevent of treat patients suffering from obesitas or from atherosclerosis, especially coronary atherosclerosis and more in general disorders which are related to atherosclerosis, such as ischaemic heart disease, peripheral vascular disease, cerebral vascular disease. The present compounds may cause regression of atherosclerosis and inhibit the clinical consequences of atherosclerosis, particularly morbidity and mortality.

In view of the utility of the compounds of formula (I), it follows that the present invention also provides a method of treating warm-blooded animals, including humans, (generally called herein patients) suffering from disorders caused by an excess of very low density lipoproteins (VLDL) or low density lipoproteins (LDL), and especially disorders caused by the cholesterol associated with said VLDL and LDL. Consequently a method of treatment is provided for relieving patients suffering from conditions, such as, for example, hyperlipidemia, obesity, atherosclerosis or type II diabetes.

Apo B-48, synthesized by the intestine, is necessary for the assembly of chylomicrons and therefore has an obligatory role in the intestinal absorption of dietary fats. The present invention provides compounds which are acting as selective MTP inhibitors at the level of the gut wall.

Additionally the present invention provides pharmaceutical compositions comprising at least one pharmaceutically acceptable carrier and a therapeutically effective amount of a compound of formula (I).

In order to prepare the pharmaceutical compositions of this invention, an effective amount of the particular compound, in base or acid addition salt form, as the active ingredient is combined in intimate admixture with at least one pharmaceutically acceptable carrier, which carrier may take a wide variety of forms depending on the form of preparation desired for administration. These pharmaceutical compositions are desirably in unitary dosage form suitable, preferably, for oral administration, rectal administration, percutaneous administration or parenteral injection.

For example in preparing the compositions in oral dosage form, any of the usual liquid pharmaceutical carriers may be employed, such as for instance water, glycols, oils, alcohols and the like in the case of oral liquid preparations such as suspensions, syrups, elixirs and solutions; or solid pharmaceutical carriers such as starches, sugars, kaolin, lubricants, binders, disintegrating agents and the like in the case of powders, pills, capsules and tablets. Because of their easy administration, tablets and capsules represent the most advantageous oral dosage unit form, in which case solid pharmaceutical carriers are obviously employed. For parenteral injection compositions, the pharmaceutical carrier will mainly comprise sterile water, although other ingredients may be included in order to improve solubility of the active ingredient. Injectable solutions may be prepared for instance by using a pharmaceutical carrier comprising a saline solution, a glucose solution or a mixture of both. Injectable suspensions may also be prepared by using appropriate liquid carriers, suspending agents and the like. In compositions suitable for percutaneous administration, the pharmaceutical carrier may optionally comprise a penetration enhancing agent and/or a suitable wetting agent, optionally combined with minor proportions of suitable additives which do not cause a significant deleterious effect to the skin. Said additives may be selected in order to facilitate administration of the active ingredient to the skin and/or be helpful for preparing the desired compositions. These topical compositions may be administered in various ways, e.g., as a transdermal patch, a spot-on or an ointment. Addition salts of the compounds of formula (I), due to their increased water solubility over the corresponding base form, are obviously more suitable in the preparation of aqueous compositions.

It is especially advantageous to formulate the pharmaceutical compositions of the invention in dosage unit form for ease of administration and uniformity of dosage. "Dosage unit form" as used herein refers to physically discrete units suitable as unitary dosages, each unit containing a predetermined amount of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions of the present invention may take the form of solid dose forms, for example, tablets (both swallowable and chewable forms), capsules or gelcaps, prepared by conventional means with pharmaceutically acceptable excipients and carriers such as binding agents (e.g. pregelatinised maize starch, polyvinylpyrrolidone, hydroxypropylmethylcellulose and the like), fillers (e.g. lactose, microcrystalline cellulose, calcium phosphate and the like), lubricants (e.g. magnesium stearate, talc, silica and the like), disintegrating agents (e.g. potato starch, sodium starch glycollate and the like), wetting agents (e.g. sodium laurylsulphate) and the like. Such tablets may also be coated by methods well known in the art.

Liquid preparations for oral administration may take the form of e.g. solutions, syrups or suspensions, or they may be formulated as a dry product for admixture with water and/or another suitable liquid carrier before use. Such liquid preparations may be prepared by conventional means, optionally with other pharmaceutically acceptable additives such as suspending agents (e.g. sorbitol syrup, methylcellulose, hydroxypropylmethylcellulose or hydrogenated edible fats), emulsifying agents (e.g. lecithin or acacia), non-aqueous carriers (e.g. almond oil, oily esters or ethyl alcohol), sweeteners, flavours, masking agents and preservatives (e.g. methyl or propyl p-hydroxybenzoates or sorbic acid).

Pharmaceutically acceptable sweeteners useful in the pharmaceutical compositions of the invention comprise preferably at least one intense sweetener such as aspartame, acesulfame potassium, sodium cyclamate, alitame, a dihydrochalcone sweetener, monellin, stevioside sucralose (4,1',6'-trichloro-4,1',6'-trideoxygalactosucrose) or, preferably, saccharin, sodium or calcium saccharin, and optionally at least one bulk sweetener such as sorbitol, mannitol, fructose, sucrose, maltose, isomalt, glucose, hydrogenated glucose syrup, xylitol, caramel or honey. Intense sweeteners are conveniently used in low concentrations. For example, in the case of sodium saccharin, the said concentration may range from about 0.04% to 0.1% (weight/volume) of the final formulation. The bulk sweetener can effectively be used in larger concentrations ranging from about 10% to about 35%, preferably from about 10% to 15% (weight/volume).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations, stronger pharmaceutically acceptable flavours may be required such as Caramel Chocolate, Mint Cool, Fantasy and the like. Each flavour may be present in the final composition in a concentration ranging from about 0.05% to 1% (weight/volume). Combinations of said strong flavours are advantageously used. Preferably a flavour is used that does not undergo any change or loss of taste and/or color under the circumstances of the formulation.

The compounds of formula (I) may be formulated for parenteral administration by injection, conveniently intravenous, intramuscular or subcutaneous injection, for example by bolus injection or continuous intravenous infusion. Formulations for injection may be presented in unit dosage form, e.g. in ampoules or multi-dose containers, including an added preservative. They may take such forms as suspensions, solutions or emulsions in oily or aqueous vehicles, and may contain formulating agents such as isotonizing, suspending, stabilizing and/or dispersing agents. Alternatively, the active ingredient may be present in powder form for mixing with a suitable vehicle, e.g. sterile pyrogen-free water, before use.

The compounds of formula (I) may also be formulated in rectal compositions such as suppositories or retention enemas, e.g. containing conventional suppository bases such as cocoa butter and/or other glycerides.

The compounds of formula (I) may be used in conjunction with other pharmaceutical agents, in particular the pharmaceutical compositions of the present invention may further comprise at least one additional lipid-lowering agent, thus leading to a so-called combination lipid-lowering therapy. The said additional lipid-lowering agent may be, for instance, a known drug conventionally used for the management of hyperlipidaemia such as e.g. a bile acid sequestrant resin, a fibric acid derivative or nicotinic acid as previously mentioned in the background of the invention. Suitable additional lipid-lowering agents also include other cholesterol biosynthesis inhibitors and cholesterol absorption inhibitors, especially HMG-CoA reductase inhibitors and HMG-CoA synthase inhibitors, HMG-CoA reductase gene expression inhibitors, CETP inhibitors, ACAT inhibitors, squalene synthetase inhibitors, CB-1 antagonists, cholesterol absorption inhibitors such as ezetimibe, and the like.

Any HMG-CoA reductase inhibitor may be used as the second compound in the combination therapy aspect of this invention. The term "HMG-CoA reductase inhibitor" as used herein, unless otherwise stated, refers to a compound which inhibits the biotransformation of hydroxymethylglutaryl-coenzyme A to mevalonic acid as catalyzed by the enzyme HMG-CoA reductase. Such "HMG-CoA reductase inhibitors" are, for example, lovastatin, simvastatin, fluvastatin, pravastatin, rivastatin, and atorvastatin.

Any HMG-CoA synthase inhibitor may be used as the second compound in the combination therapy aspect of this invention. The term "HMG-CoA synthase inhibitor" as used herein, unless otherwise stated, refers to a compound which inhibits the biosynthesis of hydroxymethylglutaryl-coenzyme A from acetyl-coenzyme A and acetoacetyl-coenzyme A, catalyzed by the enzyme HMG-CoA synthase Any HMG-CoA reductase gene expression inhibitor may be used as the second compound in the combination therapy aspect of this invention. These agents may be HMG-CoA reductase transcription inhibitors that block the transcription of DNA or translation inhibitors that prevent translation of mRNA coding for HMG-CoA reductase into protein. Such inhibitors may either affect transcription or translation directly or may be biotransformed into compounds having the above-mentioned attributes by one or more enzymes in the cholesterol biosynthetic cascade or may lead to accumulation of a metabolite having the above-mentioned activities.

Any CETP inhibitor may be used as the second compound in the combination therapy aspect of this invention. The term "CETP inhibitor" as used herein, unless otherwise stated, refers to a compound which inhibits the cholesteryl ester transfer protein (CETP) mediated transport of various cholesteryl esters and triglycerides from HDL to LDL and VLDL.

Any ACAT inhibitor may be used as the second compound in the combination therapy aspect of this invention. The term "ACAT inhibitor" as used herein, unless otherwise stated, refers to a compound which inhibits the intracellular esterification of dietary cholesterol by the enzyme acyl CoA:cholesterol acyltransferase.

Any squalene synthetase inhibitor may be used as the second compound in the combination therapy aspect of this invention. The term "squalene synthetase inhibitor" as used herein, unless otherwise stated, refers to a compound which inhibits the condensation of two molecules of farnesylpyrophosphate to form squalene, catalyzed by the enzyme squalene synthetase.

Those of skill in the treatment of hyperlipidemia will easily determine the therapeutically effective amount of a compound of formula (I) from the test results presented hereinafter. In general it is contemplated that a therapeutically effective dose will be from about 0.001 mg/kg to about 50 mg/kg of body weight, more preferably from about 0.01 mg/kg to about 5 mg/kg of body weight of the patient to be treated. It may be appropriate to administer the therapeutically effective dose in the form of two or more sub-doses at appropriate intervals throughout the day. Said sub-doses may be formulated as unit dosage forms, for example each containing from about 0.1 mg to about 350 mg, more particularly from about 1 to about 200 mg, of the active ingredient per unit dosage form.

The exact dosage and frequency of administration depends on the particular compound of formula (I) used, the particular condition being treated, the severity of the condition being treated, the age, weight and general physical condition of the particular patient as well as the other medication (including the above-mentioned additional lipid-lowering agents), the patient may be taking, as is well known to those skilled in the art. Furthermore, said effective daily amount may be lowered or increased depending on the response of the treated patient and/or depending on the evaluation of the physician prescribing the compounds of the instant invention. The effective daily amount ranges mentioned hereinabove are therefore only guidelines.

EXPERIMENTAL PART

In the procedures described hereinafter the following abbreviations were used: "ACN" stands for acetonitrile; "DCM" stands for dichloromethane; "DMF" means N,N-dimethyl-formamide; "THF" stands for tetrahydrofuran; and "DIPE" stands for diisopropylether.

N-cyclohexylcarbodiimide N-methyl polystyrene HL resin (1.90 mmole/g) is a Novabiochem 01-64-021 resin; polymer-supported carbonate base [polystyrylmethyl]-trimethyl ammonium bicarbonate resin (5.8 mmole/g) is a Novabiochem 01-64-041 resin; polystyrene-carbodiimide resin (1.90 mmol/g) is a Novabiochem 01-64-024 resin; polystyrene-N-methyl morpholine HL (3.80 mmol/g) resin is a Novabiochem 01-64-0211 resin; polystyrene-bicarbonate (5.8 mmol/g) resin is a Novabiochem-01-064-0419 resin.

The Novabiochem resins can be obtained from Calbiochem-Novabiochem AG, Weidenmattweg 4, CH-4448 Läufelfingen, Switzerland.

A. Synthesis of the Intermediates

Example A.1 a) Preparation of

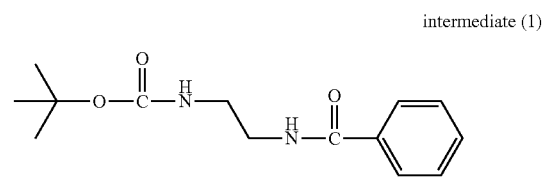

intermediate (1)

Benzenecarboxylic acid (0.00012 mol, 1.2 equivalents) was dissolved in DMF (0.5 ml) and mixed with a N-cyclohexylcarbodiimide N-methyl polystyrene HL resin (1.90 mmol/g) (0.10526 g, 0.0002 mol, 2 equivalents). 1-Hydroxybenzotriazole (HOBT) (0.02027 g, 0.00015 mol, 1.5 equiv) in DMF (0.5 ml) was added. The mixture was stirred for 15 minutes, followed by the addition of N-(tert-butoxycarbonyl)-1,2-ethanediamine (0.0001 mol) in DCM (3 ml). After completion of the reaction, a polymer-supported carbonate base [polystyrylmethyl]trimethyl ammonium bicarbonate resin (5.8 mmole/g) (0.076 g, 0.00045 mol, 4.5 equivalents) was added and the mixture was stirred for 3 hours. Finally, the resins were removed by filtration and washed three times with a mixture of DCM/DMF (3/1 v/v, 1.0 ml), followed by evaporation of the solvents under reduced pressure, thereby yielding intermediate (1) (quantitative yield; used in next reaction step, without further purification).

b) Preparation of

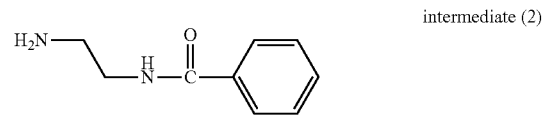

intermediate (2)

Intermediate (1) (0.0001 mol) was dissolved in a mixture of 6N HCl in isopropanol (2 ml) and stirred and heated for 5 hours at 65° C. The reaction mixture was concentrated under reduced pressure, thereby yielding intermediate (2) as its hydrochloric acid addition salt.

In an analogous way, intermediate (3) to intermediate (8) were prepared in the form of their hydrochloric acid salts. To that effect, in reaction step a) benzenecarboxylic acid was replaced by 2-methoxybenzenecarboxylic acid, or 4'-(trifluoromethyl)-2-biphenylcarboxylic acid; and N-(tert-butoxycarbonyl)-1,2-ethanediamine was replaced by N-(tert-butoxycarbonyl)-1,3-propanediamine, N-methyl-N-(tert-butoxycarbonyl)-1,2-ethanediamine or N-methyl-N-(tert-butoxycarbonyl)-1,3-propanediamine.

intermediate (3)
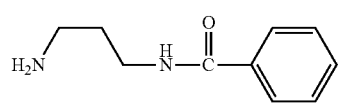

intermediate (4)
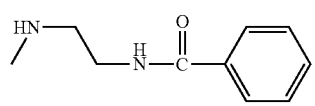

intermediate (5)
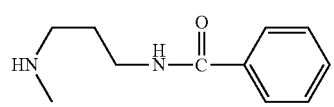

intermediate (6)
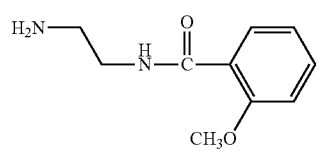

intermediate (7)
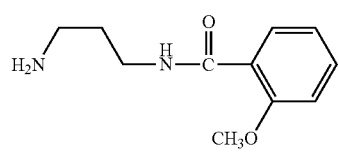

intermediate (8)
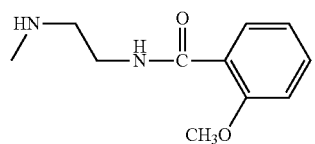

intermediate (9)
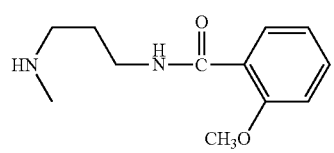

intermediate (10)
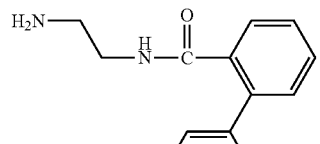

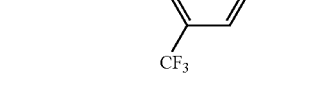

intermediate (11)
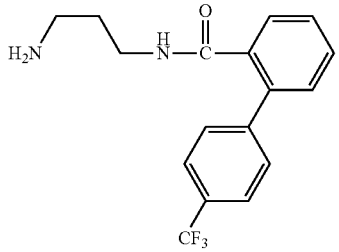

intermediate (12)
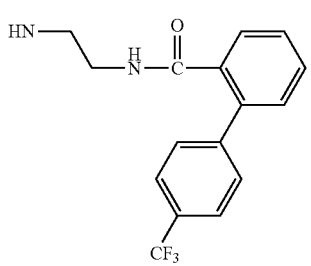

intermediate (13)
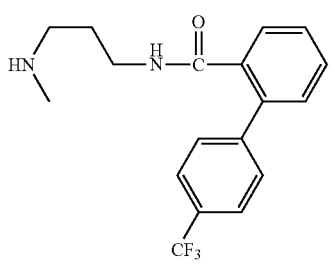

Example A.2

Preparation of intermediate (14)
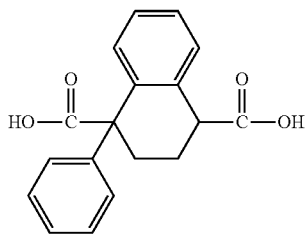

2-Hydroxy-2-phenyl-propionic acid methyl ester (0.1 mol) was added to a solution of sulfuric acid (300 ml) in water (250 ml) and the reaction mixture was stirred at 100° C. for 20 hours. The precipitate was filtered off and dissolved in DCM (600 ml). The organic layer was separated, dried, filtered and the solvent was evaporated until a volume of 100 ml. The precipitate was filtered off and dried, yielding 9 g of intermediate (14).

Example A.3

Preparation of

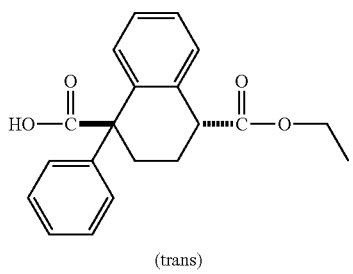

intermediate (15)

(trans)

A mixture of intermediate (14) (1.327 mol) in dry ethanol (2360 ml) was stirred and concentrated sulfuric acid (4 ml) was added. The reaction mixture was refluxed for 22 hours under nitrogen and then the reaction mixture was allowed to cool overnight to room temperature. The resulting precipitate was filtered off, washed with dry ethanol and dried, yielding 120 g of intermediate (15) (mp. 186-187° C.).

The ethanol-layers were combined and evaporated, and the resulting residue was dissolved in DCM (1450 ml), washed with an aqueous NaHCO$_3$ solution (twice with 500 ml), dried and the solvent was evaporated. The residue was stirred in DIPE (680 ml) at a temperature of 50-55° C. and the residual DCM was distilled off and the concentrate was left to stand for more than 2 hours at room temperature. The resulting solids were filtered off, washed with DIPE (120 ml) and with pentane and then dried at 40° C., yielding another 103.2 g of intermediate (15) (mp. 187-188° C.).

Preparation of

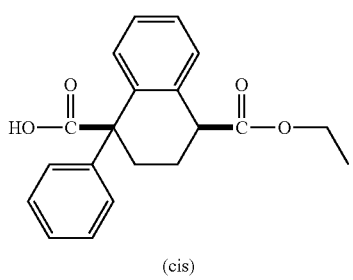

intermediate (16)

(cis)

The previous DIPE/pentane layers were evaporated and the residue was dissolved in dry ACN (200 ml), then the solvent was evaporated again, yielding 166.3 g of intermediate (16) (mp. 75° C.).

Example A.4

Preparation of

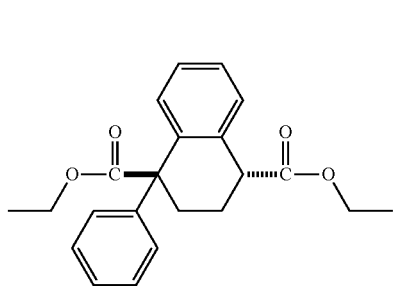

intermediate (17)

Intermediate (15) (0.03 mol) was stirred in chloroform (50 ml). Thionyl chloride (0.06 mol) was added and the reaction mixture was stirred and refluxed for 4 hours until gas evolution ceased. The reaction mixture was concentrated by evaporation of the solvent. Chloroform (200 ml) was added and the solvent was evaporated again, yielding a residue that was slowly added to dry ethanol (100 ml) which was cooled on an ice-water bath at ±5° C. The ice-bath was removed and reaction mixture was allowed to warm to room temperature. The reaction mixture was stirred for 4 hours at room temperature. The solvent was evaporated, yielding intermediate (17) (mp: 78-80° C.).

Intermediate (18) was prepared analogously but starting from intermediate (16).

Preparation of

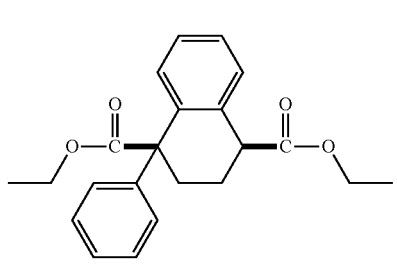

intermediate (18)

Example A.5

Preparation of

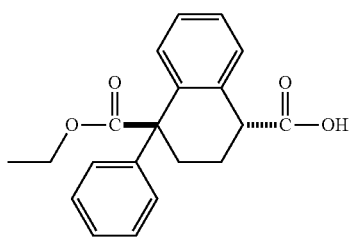

intermediate (19)

A mixture of intermediate (17) (0.0567 mol) and p-toluene sulfonic acid (1 g) was stirred and refluxed in a mixture of formic acid (500 ml) and concentrated HCl (125 ml) for 3 hours. The reaction mixture was concentrated by evaporation of the solvent, the residue was dissolved in DCM, washed with an aqueous NaHCO$_3$ solution and dried. The solvent was evaporated and the residue was purified by column chromatography on silica (eluent:ethyl acetate/hexane 1/9), yielding intermediate (19) (mp. 115-118° C.).

Intermediate (20) (mp. 133-135° C.) was prepared analogously but starting from intermediate (18).

Preparation of

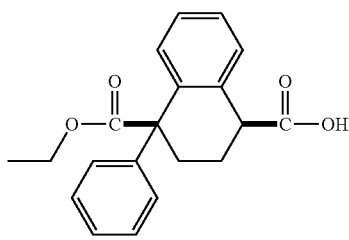

intermediate (20)

Example A.6 a) Preparation of

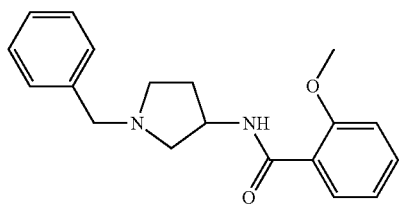

intermediate (21)

2-Methoxy-benzoic acid (0.028 mol) was dissolved in DCM (150 ml). Thionyl chloride (8.2 ml) was added dropwise to this mixture and the mixture was refluxed for 2 hours and 30 minutes. The reaction mixture was cooled and the solvent was evaporated. Then DCM (150 ml) was added and the solvent was evaporated again. The crude compound was dissolved in DCM (150 ml). First 1-(phenylmethyl)-3-pyrrolidinamine (0.028 mol) was added and then a saturated aqueous NaHCO$_3$ solution (75 ml) was added. The mixture was reacted for 2 hours. Then the layers were separated. The separated organic layer was dried (MgSO$_4$), filtered and the solvent was evaporated. The residue was worked up in diisopropyl ether and the crude compound was purified by column chromatography (eluent: from 100% CH$_2$Cl$_2$ till 3% CH$_3$OH/CH$_2$Cl$_2$). The product fractions were collected and the solvent was evaporated, yielding 7.14 g of intermediate (21).

b) Preparation of

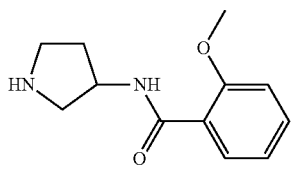

intermediate (22)

A mixture of intermediate (21) (0.023 mol) in CH$_3$OH (150 ml) was hydrogenated with palladium-on-carbon 10% (1 g) as a catalyst. After uptake of hydrogen (1 equivalent), the catalyst was filtered off and the filtrate was evaporated. The residue was purified by reversed-phase high-performance liquid chromatography (Shandon Hyperprep® C18 BDS (Base Deactivated Silica) 8 μm, 250 g, I.D. 5 cm). A gradient with two or three mobile phases was applied (phase A: a 0.25% NH$_4$HCO$_3$ solution in water; phase B: CH$_3$OH (optional); phase C: CH$_3$CN). The product fractions were collected and the solvent was evaporated, yielding 2.56 g of intermediate (22).

Example A.7 a) Preparation of

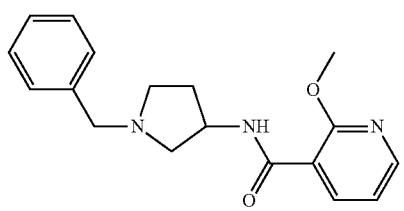

intermediate (23)

2-Methoxy-3-pyridinecarboxylic acid (0.028 mol) was dissolved in DCM (150 ml). Thionyl chloride (8.2 ml; 0.112 mol)) was added dropwise to this mixture and the mixture was refluxed for 2 hours and 30 minutes. The solvent was evaporated. Then DCM (150 ml) was added and the solvent was evaporated again. The crude compound was dissolved in DCM (150 ml). First 1-(phenylmethyl)-3-pyrrolidinamine (0.028 mol) was added and then a saturated aqueous NaHCO$_3$ solution (75 ml) was added. The mixture was reacted for 2 hours. Then, the layers were separated. The separated organic layer was dried (MgSO$_4$), filtered and the solvent was evaporated. The residue was purified by column chromatography (eluent: from 100% CH$_2$Cl$_2$ till CH$_3$OH/CH$_2$Cl$_2$ 1/100). The product fractions were collected and the solvent was evaporated, yielding 7.97 g of intermediate (23).

b) Preparation of

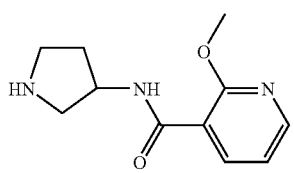

intermediate (24)

A mixture of intermediate (23) (0.026 mol) in CH$_3$OH (150 ml) was hydrogenated with palladium-on-carbon 10% (1 g) as a catalyst. After uptake of hydrogen (1 equivalent), the catalyst was filtered off and the filtrate was evaporated. The residue was purified by reversed-phase high-performance liquid chromatography (Shandon Hyperprep® C18 BDS (Base Deactivated Silica) 8 μm, 250 g, I.D. 5 cm). A gradient with two or three mobile phases was applied (phase A: a 0.25% NH$_4$HCO$_3$ solution in water: phase B: CH$_3$OH (optional); phase C: CH$_3$CN). The product fractions were collected and the solvent was evaporated, yielding 3.01 g of intermediate (24).

Example A.8 a) Prepration of

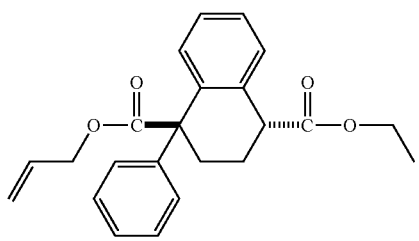

intermediate (25)

A solution of trans-1-phenyl-1,2,3,4-tetrahydro-naphthalene-1,4-dicarboxylic acid 4-ethyl ester (0.15 mol) in NaHCO$_3$ (0.15 M in 200 ml water) was stirred and Aliquat™ (0.15 mol) (a mixture of tri-C$_{8-10}$-alkylmethyl quaternary ammonium chlorides) and 3-bromo-1-propene (0.75 mol) in DCM (200 ml) was added, then the reaction mixture was stirred for 4 days at 20° C. and the organic layer was separated. The aqueous layer was extracted with DCM (300 ml) and the combined organic layers were dried (MgSO$_4$). The solvent was evaporated and the residue was stirred in hexane (500 ml), then cooled to 0° C. The resulting precipitate was filtered off, washed with hexane and dried overnight at 60° C., yielding 46 g of intermediate (25).

b) Preparation of

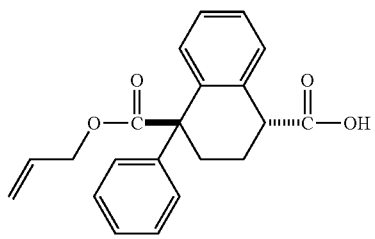

intermediate (26)

Concentrated hydrochloric acid (28%) (100 ml) and 4-methyl-benzenesulfonic acid (0.7 g) were added to a solution of intermediate (25) (0.13 mol) in formic acid (400 ml), then the reaction mixture was stirred and refluxed for 6 hours. The solvent was evaporated and the residue was partitioned between DCM (300 ml) and a saturated aqueous NaHCO$_3$ solution (200 ml). The DCM-layer was separated, dried (MgSO$_4$) and the solvent was evaporated. The residue was triturated under ether to give Solid (I) and the mother layers were concentrated, then crystallised from a ethyl acetate/hexane mixture to give Solid (II). Solids (I) and (II) were combined and purified by flash column chromatography (eluent: DCM/CH$_3$OH 95/5). The product fractions were collected, the solvent was evaporated and the residue was triturated under hexane. This residue was then triturated under ether and filtered off, to give a solid, yielding 7 g of intermediate (26) (mp. 138-139° C.).

Example A.9 a) Preparation of

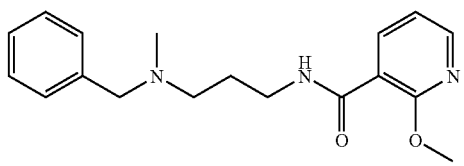

intermediate (27)

2-Methoxy-3-pyridinecarboxylic acid (0.028 mol) was dissolved in DCM (150 ml). Thionyl chloride (8 ml; 0.112 mol) was added dropwise to this mixture and the mixture was refluxed for 2 hours and 30 minutes. The solvent was evaporated. Then DCM (150 ml) was added and the solvent was evaporated again. The crude compound was dissolved in DCM (150 ml). First N-methyl-N-(phenylmethyl)-1,3-propanediamine (0.028 mol) was added and then a saturated aqueous NaHCO$_3$ solution (75 ml) was added. The mixture was reacted for 2 hours. Then, the layers were separated. The separated organic layer was dried (MgSO$_4$), filtered and the solvent was evaporated. The residue was purified by column chromatography (eluent: from 100% CH$_2$Cl$_2$ till CH$_3$OH/CH$_2$Cl$_2$ 1/100). The product fractions were collected and the solvent was evaporated, yielding 8.71 g of intermediate (27).

b) Preparation of

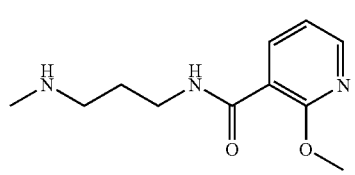

intermediate (28)

A mixture of intermediate (27) (0.028 mol) in CH$_3$OH (150 ml) was hydrogenated with palladium-on-carbon 10% (2 g) as a catalyst. After uptake of hydrogen (1 equivalent), the catalyst was filtered off and the filtrate was evaporated. The residue was crystallized from 2-propanol with addition of HCl (6 N) in 2-propanol. The residue was purified by reversed-phase high-performance liquid chromatography (Shandon Hyperprep® C18 BDS (Base Deactivated Silica) 8 µm, 250 g, I.D. 5 cm). A gradient with two or three mobile phases was applied (phase A: a 0.25% NH$_4$HCO$_3$ solution in water; phase B: CH$_3$OH (optional); phase C: CH$_3$CN). The product fractions were collected and the solvent was evaporated, yielding 2.65 g of intermediate (28).

Example A.10 a) Preparation of

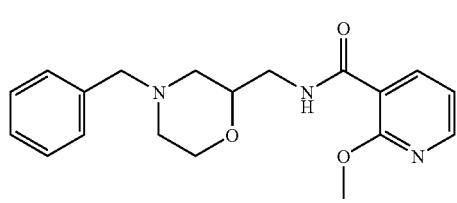

intermediate (29)

2-Methoxy-3-pyridinecarboxylic acid (0.00485 mol) was dissolved in DCM (50 ml). Thionyl chloride (1.4 ml) was added dropwise to this mixture and the mixture was refluxed for 2 hours and 30 minutes. The solvent was evaporated. Then DCM (50 ml) was added and the solvent was evaporated again. The crude compound was dissolved in DCM (50 ml). First 4-(phenylmethyl)-2-morpholinemethanamine (0.00485 mol) was added and then a saturated aqueous NaHCO$_3$ solution (25 ml) was added. The mixture was reacted for 2 hours. Then, the layers were separated. The separated organic layer was dried (MgSO$_4$), filtered and the solvent was evaporated. The residue was purified by column chromatography (eluent: from 100% CH$_2$Cl$_2$ till CH$_3$OH/CH$_2$Cl$_2$ 1/100). The product fractions were collected and the solvent was evaporated, yielding 1.6 g of intermediate (29).

b) Preparation of

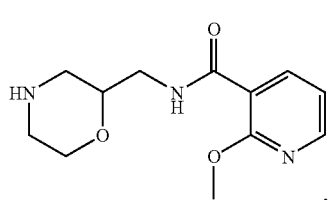

intermediate (30)
·HCl

A mixture of intermediate (29) (0.0049 mol) in CH$_3$OH (50 ml) was hydrogenated with palladium-on-carbon (0.4 g) as a catalyst. After uptake of hydrogen (1 equivalent), the catalyst was filtered off and the filtrate was evaporated. The residue was crystallized from 2-propanol with addition of HCA (6 N) in 2-propanol. The product was filtered off and dried, yielding 0.8 g of intermediate (30), isolated as a hydrochloric acid salt.

Example A.11 a) Preparation of

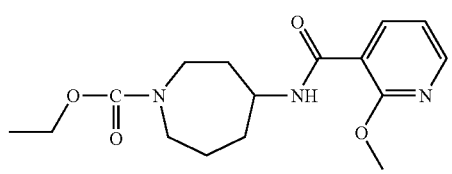

intermediate (31)

2-Methoxy-3-pyridinecarboxylic acid (0.0269 mol) was dissolved in DCM (150 ml). Thionyl chloride (8 ml) was added dropwise to this mixture and the mixture was refluxed for 2 hours and 30 minutes. The solvent was evaporated. Then DCM (150 ml) was added and the solvent was evaporated again. The crude compound was dissolved in DCM (150 ml). First 4-aminohexahydro-1H-azepine-1-carboxylic acid, ethyl ester (0.0269 mol) was added and then a saturated aqueous NaHCO$_3$ solution (75 ml) was added. The mixture was reacted for 2 hours. Then, the layers were separated. The separated organic layer was dried (MgSO$_4$), filtered and the solvent was evaporated. The residue was purified by column chromatography (eluent: from 100% CH$_2$Cl$_2$ till CH$_3$OH/CH$_2$Cl$_2$ 1/100). The product fractions were collected and the solvent was evaporated, yielding 8.63 of intermediate (31).

b) Preparation of

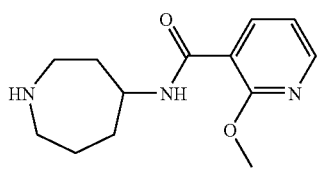

intermediate (32)

Intermediate (31) (0.026 mol) was dissolved in CH₃OH (60 ml). Potassium hydroxide (7 g) was added and the reaction mixture was refluxed for 5 hours. DCM was added to the reaction mixture and the organic layer was washed two times with water. The separated organic layer was dried (MgSO₄), filtered and the solvent was evaporated. The residue was purified by reversed-phase high-performance liquid chromatography (Shandon Hyperprep® C18 BDS (Base Deactivated Silica) 8 μm, 250 g, I.D. 5 cm). A gradient with two or three mobile phases was applied (phase A: a 0.25% NH₄HCO₃ solution in water; phase B: CH₃OH (optional); phase C: CH₃CN). The product fractions were collected and the solvent was evaporated, yielding 2.01 g of intermediate (32).

Example A.12 a) Preparation of

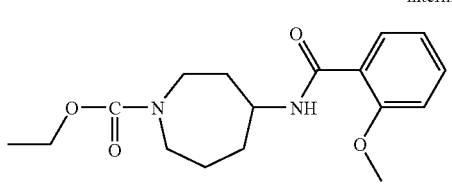

intermediate (33)

2-Methoxy-benzoic acid (0.0269 mol) was dissolved in DCM (150 ml). Thionyl chloride (8 ml) was added dropwise to this mixture and the mixture was refluxed for 2 hours and 30 minutes. The solvent was evaporated. Then DCM (150 ml) was added and the solvent was evaporated again. The crude compound was dissolved in DCM (150 ml). First 4-amino-hexahydro-1H-azepine-1-carboxylic acid, ethyl ester (0.0269 mol) was added and then a saturated aqueous NaHCO₃ solution (75 ml) was added. The mixture was reacted for 2 hours. Then, the layers were separated. The separated organic layer was dried (MgSO₄), filtered and the solvent was evaporated. The residue was purified by column chromatography (eluent: from 100% CH₂Cl₂ till CH₃OH/CH₂Cl₂ 1/100). The product fractions were collected and the solvent was evaporated, yielding 8.5 g of intermediate (33).

b) Preparation of

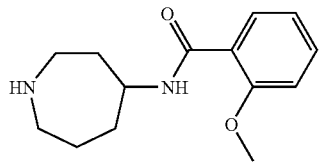

intermediate (34)

Intermediate (33) (0.0262 mol) was dissolved in CH₃OH (120 ml) and water (1 ml) was added. Then sodium hydroxide (7 g) was added and the reaction mixture was refluxed for 72 hours. The solvents were evaporated and water and DCM were added. The organic layer was washed with water. The separated organic layer was dried (MgSO₄), filtered and the solvent was evaporated. The residue was purified by reversed-phase high-performance liquid chromatography (Shandon Hyperprep® C18 BDS (Base Deactivated Silica) 8 μm, 250 g, I.D. 5 cm). A gradient with two or three mobile phases was applied (phase A: a 0.25% NH₄HCO₃ solution in water; phase B: CH₃OH (optional); phase C: CH₃CN). The product fractions were collected and the solvent was evaporated, yielding 4.02 g of intermediate (34).

B. Preparation of the Final Compounds

Example B.1

A mixture of intermediate (2) (0.0001 mol), a polystyrene-carbodiimide (1.90 mmol/g) resin (0.0002 mol, 0.105 g), a polystyrene-N-methyl morpholine HL (3.80 mmol/g) resin (0.0005 mol, 0.132 g), a solution of intermediate (19) (0.00015 mol) in DCM (1 ml) and 1-hydroxybenzotriazole (HOBT) (0.0015 mol, 0.020 g) in THF (1 ml) was shaken overnight at room temperature. A polystyrene-bicarbonate (5.8 mmol/g) resin (0.0005 mol, 0.086 g) was added as a scavenger to remove excess of HOBT. The reaction mixture was shaken for two hours, filtered, and the filtrate was evaporated, yielding compound (I).

Example B.2

DMF (3 drops) was added to a solution of intermediate (19) (0.025 mol) in DCM (100 ml) and then thionylchloride (0.1 mol) was added. The reaction mixture was stirred and refluxed for 1 hour and then the solvent was evaporated. DCM was added and the solvent was evaporated. The resulting residue was dissolved in DCM (100 ml) and then intermediate (7) (0.025 mol) was added, followed by an aqueous NaHCO₃ solution (50 ml). The reaction mixture was stirred or 4 hours at room temperature and the layers were separated. The organic layer was dried and the solvent was evaporated. The residue was separated into its enantiomers by high-performance liquid chromatography (Chiralpak AD) (eluent: hexane/ethanol 80/20). Two product fractions were collected and the solvent was evaporated. The residues were each triturated under DIPE and then the desired products were collected, yielding 4.84 g of compound (25) and 4.72 g of compound (26).

Example B.3

A solution of intermediate (19) (0.025 mol) in DCM (100 ml) was stirred and refluxed with thionylchloride (0.1 mol) for 1 hour and then the solvent was evaporated. Fresh DCM was added and the excess of thionylchloride was removed by evaporation. The residue was dissolved in DCM (50 ml) and the resulting solution was added to a mixture of intermediate (9) (0.025 mol) in DCM (50 ml). An aqueous $NaHCO_3$ solution (50 ml) was added and the reaction mixture was stirred for 2 hours at room temperature. The layers were separated, and the organic layer was washed with diluted HCl, dried and the solvent was evaporated. The obtained residue was separated into its enantiomers by HPLC-purification (Chiral phase AD) (eluent: hexane/ethanol 60/40), yielding 5.02 g of compound (27) and 5.05 g of compound (28).

Example B.4

Intermediate (26) (1 g; 0.0030 mol) was dissolved in DCM (15 ml). Thionyl chloride (0.54 ml; 0.0075 mol) was added dropwise to this solution and a few drops of DMF were added. The reaction was refluxed for 1 hour. The solvent was evaporated. DCM (15 ml) was added to the residue and the solvent was evaporated again. The crude mixture was dissolved in DCM (15 ml) and first intermediate (9) (0.003 mol) and then $NaHCO_3$ saturated aqueous (15 ml) were added. The reaction mixture was stirred for 2 hours at room temperature. The layers were separated. The separated organic layer was dried ($MgSO_4$), filtered and the solvent was evaporated, yielding 1.6 g of compound (34).

Example B.5

Compound (38) (0.00297 mol) was dissolved in THF (20 ml). The reaction was bubbled with nitrogen and then tetrakis(triphenylphosphine)palladium (0.070 g) was added. The mixture was cooled to 0° C. with an ice-bath and then sodium borohydride (0.00297 mol) was added. Cooling was continued for 4 hours and the mixture was reacted overnight at room temperature. Then the reaction was quenched with HCl (1 N) and extracted with DCM. The separated organic layer was dried ($MgSO_4$), filtered and the solvent was evaporated. The product was purified by column chromatography (eluent: ($CH_2Cl_2/CH_3OH$) from 99/1 till 90/10). The product fractions were collected and the solvents were evaporated in vacuo. The residue was redissolved in $CH_2Cl_2/CH_3OH$ and treated with activated charcoal. The mixture was filtered over decalite and the solvent was evaporated. The residue was purified by reversed-phase high-performance liquid chromatography (Shandon Hyperprep® C18 BDS (Base Deactivated Silica) 8 μm, 250 g, I.D. 5 cm). A gradient with two or three mobile phases was applied (phase A: a 0.25% $NH_4HCO_3$ solution in water; phase B: $CH_3OH$ (optional); phase C: $CH_3CN$). The pure fractions were collected and the solvent was evaporated. The residue was redissolved in DCM and the solution was added to diisopropyl ether. The precipitate was filtered off and the solid was dried, yielding 0.016 g of compound (29).

Example B.6 a) Compound (34) (0.0030 mol) was dissolved in THF (20 ml). The reaction was bubbled with nitrogen and then tetrakis(triphenylphosphine)palladium (0.00006 mol) was added. The mixture was cooled to 0° C. with an ice-bath and then sodium borohydride (0.003 mol) was added. Cooling was continued for 4 hours and the mixture was reacted overnight at room temperature. Then the reaction was quenched with HCl (1 N) and extracted with DCM. The separated organic layer was dried ($MgSO_4$), filtered and the solvent was evaporated. The product was purified by column chromatography (eluent: (DCM/MeOH) from 99/1 till 90/10). The product fractions were collected and the solvents were evaporated in vacuo. The residue was redissolved in $CH_2Cl_2/CH_3OH$ and treated with activated charcoal. The mixture was filtered over decalite and the solvent was evaporated. The residue was purified by reversed-phase high-performance liquid chromatography (Shandon Hyperprep® C18 BDS (Base Deactivated Silica) 8 μm, 250 g, I.D. 5 cm). A gradient with two or three mobile phases was applied (phase A: a 0.25% $NH_4HCO_3$ solution in water; phase B: $CH_3OH$ (optional); phase C: $CH_3CN$). The product fractions were collected and the solvent was evaporated. The residue was dissolved in DCM and this solution was added to diisopropyl ether. The precipitate was filtered off and the white solid was dried, yielding trans-4-{[3-(2-methoxy-benzoylamino)-propyl]-methyl-carbamoyl}-1-phenyl-1,2,3,4-tetrahydro-naphthalene-1-carboxylic acid (intermediate (35)).

b) Intermediate (35) (0.000199 mol, 0.100 g) was dissolved in dry DCM (2 ml). Then 1-hydroxy-1H-benzotriazole (1.2 equivalent, 0.032 g), N'-(ethylcarbonimidoyl)-N,N-dimethyl-1,3-propanediamine, monohydrochloride (1.2 eq, 0.046 g) and methyl 3-aminopropanoate hydrochloride (3 equivalents, 0.083 g) and N-ethyl-N-(1-methyl-ethyl)-2-propanamine (10 equivalents, 0.329 ml) were added to the mixture. The reaction mixture was stirred at room temperature overnight. Extra methyl 3-amino-propanoate hydrochloride (3 equivalents, 0.083 g) was added and the mixture was washed 3 times with a saturated aqueous solution of $NaHCO_3$. The separated organic layer was dried ($MgSO_4$), filtered and the solvent was evaporated. The residue was then purified by column chromatography (100% $CH_2Cl_2$ till 2% $CH_3OH/CH_2Cl_2$). The desired fractions were collected and the solvent was evaporated, yielding compound (31).

Example B.7

Intermediate (19) (0.00376 mol, 1.22 g) was dissolved in dry DCM (20 ml). Then HOBt (0.00451 mol, 0.733 g), 1-ethyl-3-(3'-dimethyl-aminopropyl)carbodiimide hydrochloride (EDCI) (0.00451 mol, 1.04 g), and intermediate (24) (0.00451 mol) and DIPEA (0.0376 mol, 7.4 ml) were added to the mixture. The reaction mixture was stirred at room temperature overnight. Extra intermediate (24) (0.00451 mol) was added and the mixture was washed 3 times with a saturated aqueous solution of NaHCO3. The separated organic layer was dried, filtered and the solvent was evaporated. The residue was then purified by flash column chromatography (from 100% $CH_2Cl_2$ to CH3OH/CH2Cl2 1/20). The desired product fraction was collected and the solvent was evaporated, yielding compound (45).

Table F-1 lists the compounds that were prepared according to one of the above Examples. The stereochemical configuration for some compounds has been designated as R*, or S* indicating a relative stereochemistry when the absolute stereochemistry is unknown although the compound itself has been isolated as a single stereoisomer and is therefore enantiomerically pure. For some compounds the melting point (m.p.) has been included.

TABLE F-1
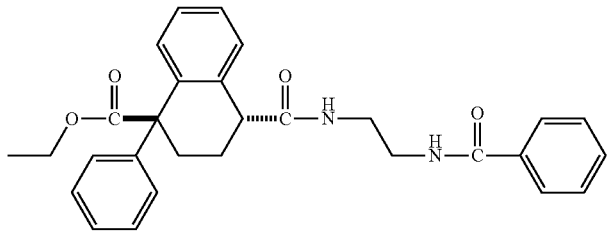
Co. No. 1; Ex. B.1; trans
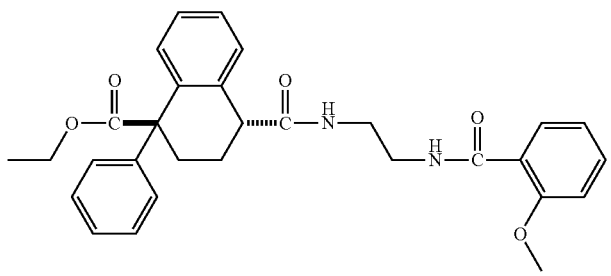
Co. No. 2; Ex. B.1; trans
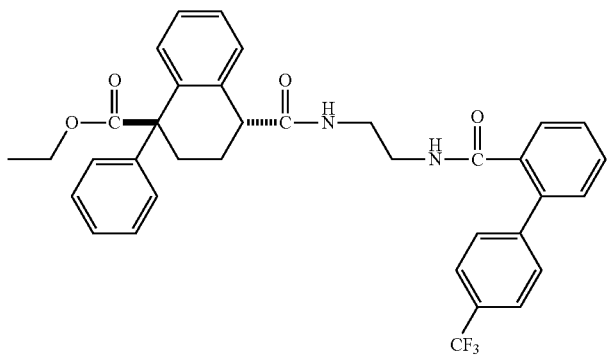
Co No. 3; Ex. B.1; trans
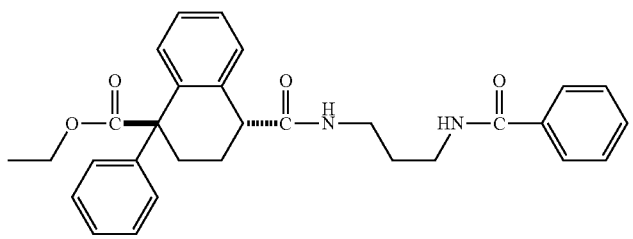
Co No. 4; Ex. B.1; trans
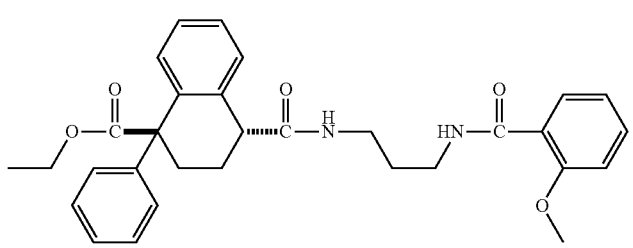
Co No. 5; Ex. B.1; trans TABLE F-1-continued
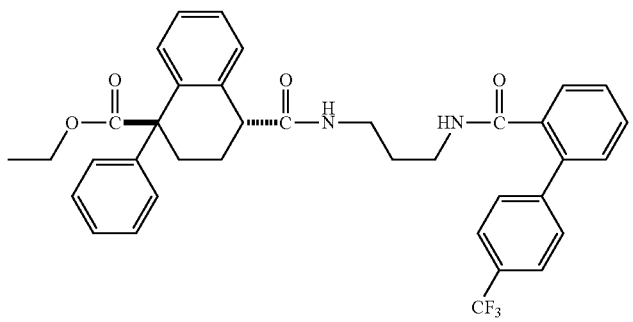
Co No. 6; Ex. B.1; trans
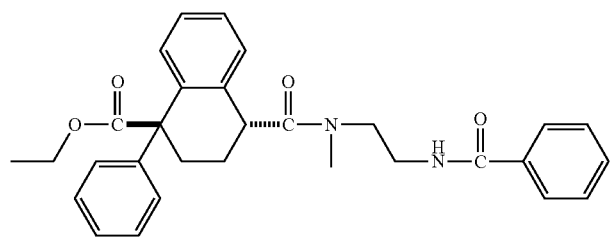
Co No. 7; Ex. B.1; trans
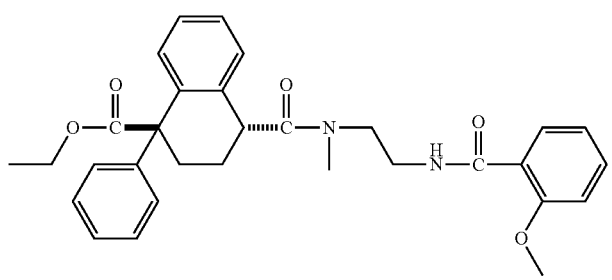
Co No. 8; Ex. B.1; trans
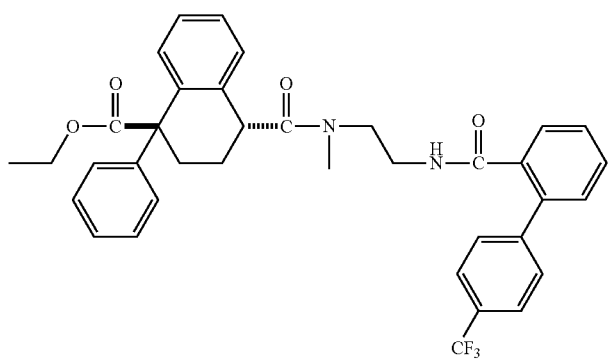
Co No. 9; Ex. B.1; trans
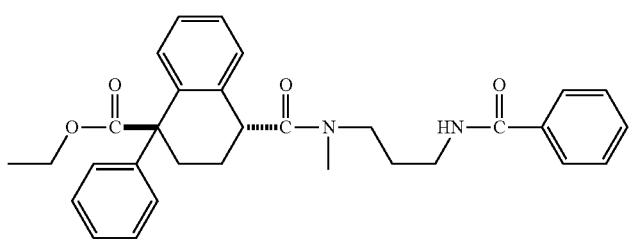
Co No. 10; Ex. B.1; trans TABLE F-1-continued
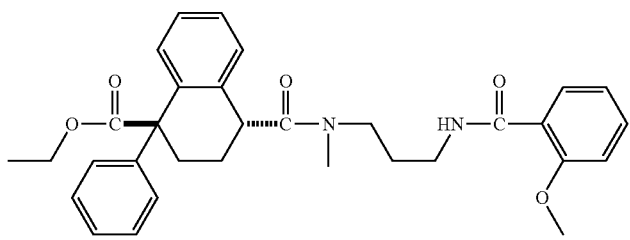
Co No. 11; Ex. B.1; trans
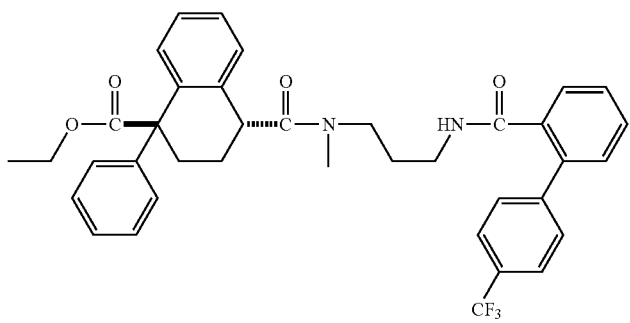
Co No. 12; Ex. B.1; trans
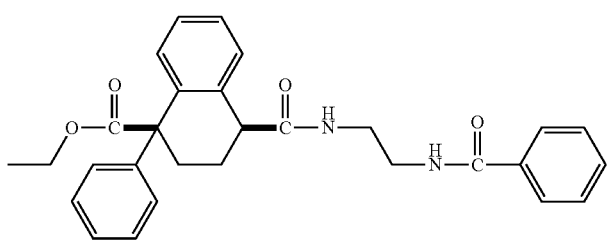
Co No. 13; Ex. B.1; cis
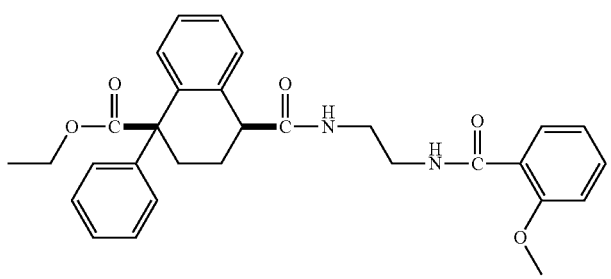
Co No. 14; Ex. B1; cis
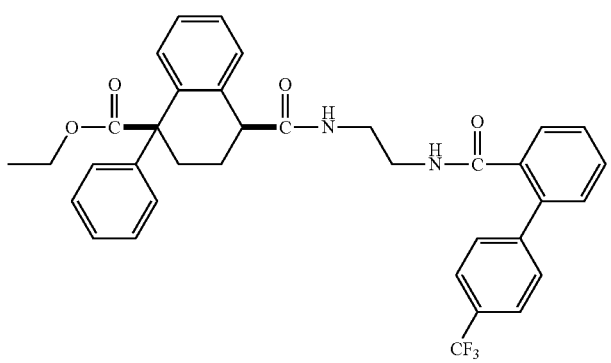
Co No. 15; Ex. B.1; cis TABLE F-1-continued
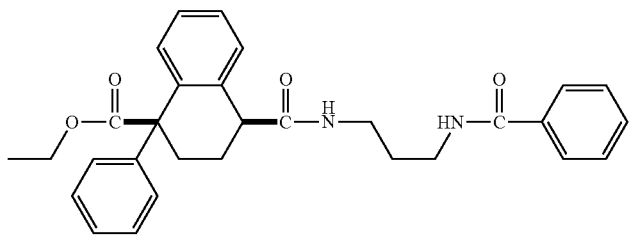
Co No. 16; Ex. B.1; cis
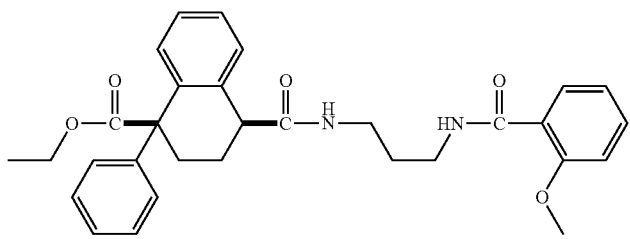
Co No. 17; Ex. B.1; cis
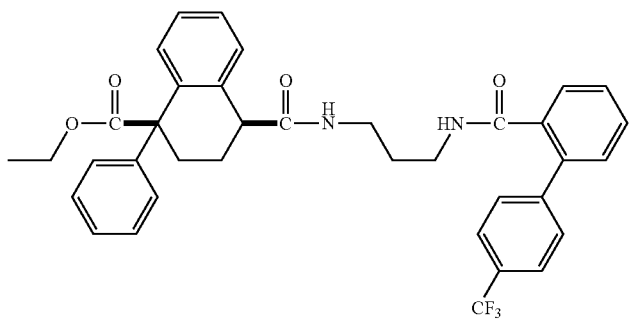
Co No. 18; Ex. B.1; cis
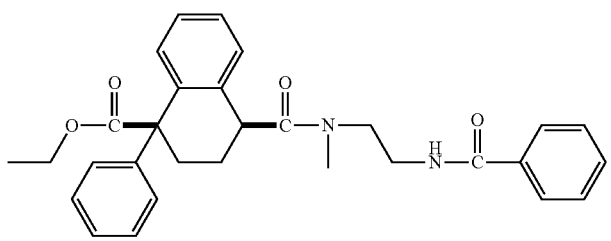
Co No. 19; Ex. B.1; cis
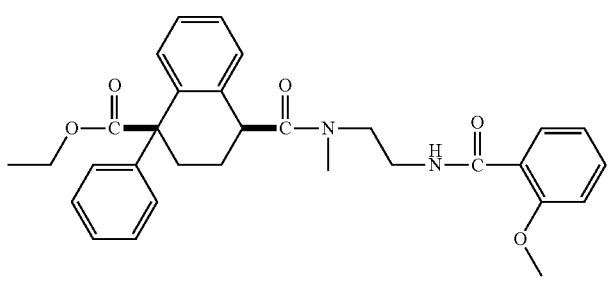
Co No. 20; Ex. B.1; cis TABLE F-1-continued
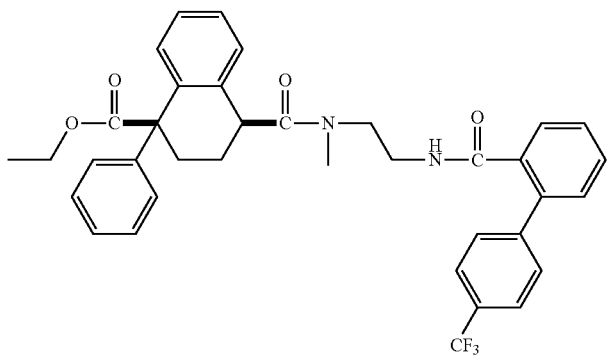
Co No. 21; Ex. B.1; cis
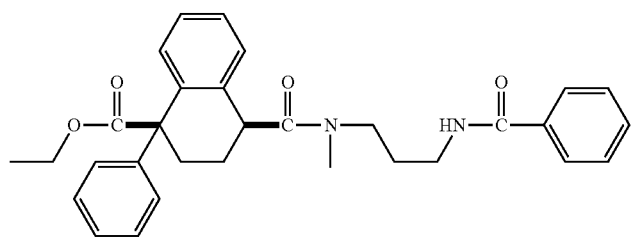
Co No. 22; Ex. B.1; cis
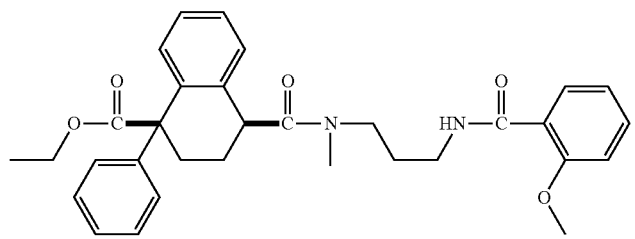
Co No. 23; Ex. B.1; cis
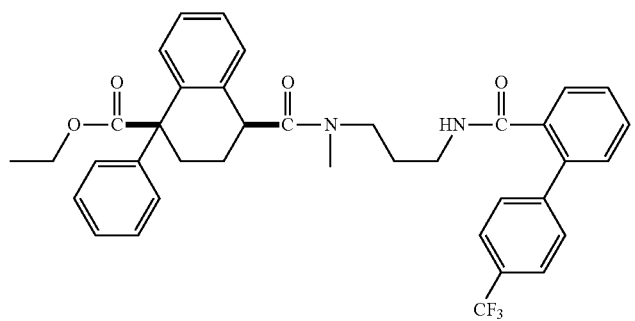
Co No. 24; Ex. B.1; cis
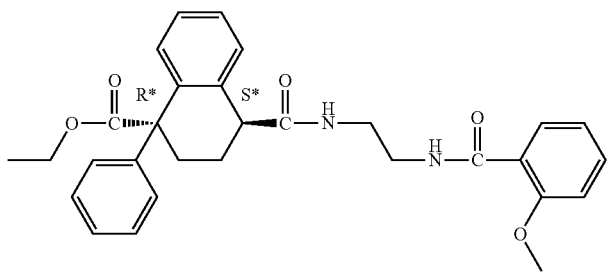
Co No. 25; Ex. B.2; (R*, S*); mp. 166.4-167.8° C. (Büchi visual)

TABLE F-1-continued
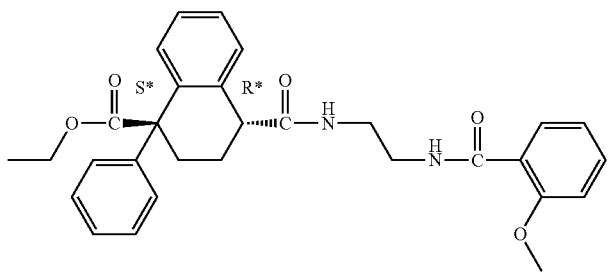
Co No. 26; Ex. B.2; (S*, R*); m.p. 165.1-
166.3° C.; (Büchi visual)
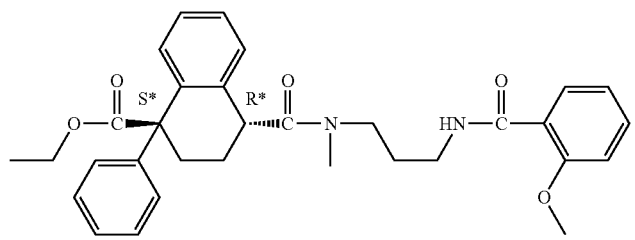
Co No. 27; Ex. B.3; (S*, R*)
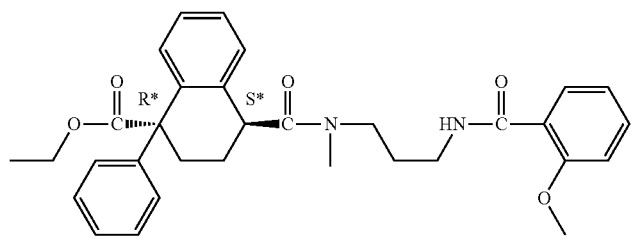
Co No. 28; Ex. B.3; (R*, S*)
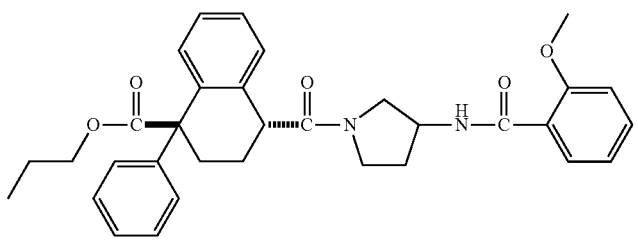
Co No. 29; Ex. B.5
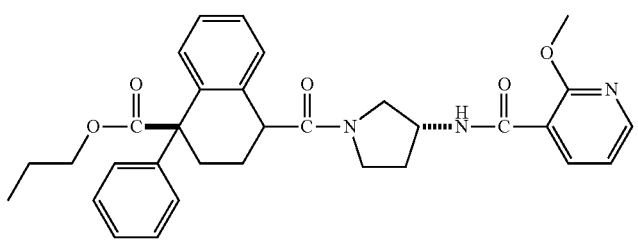
Co No. 30; Ex. B.5; trans
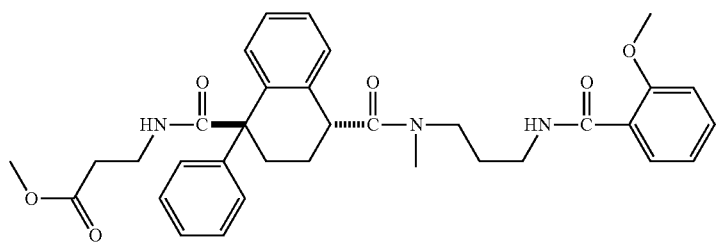
Co. No. 31; Ex. B.6; trans TABLE F-1-continued
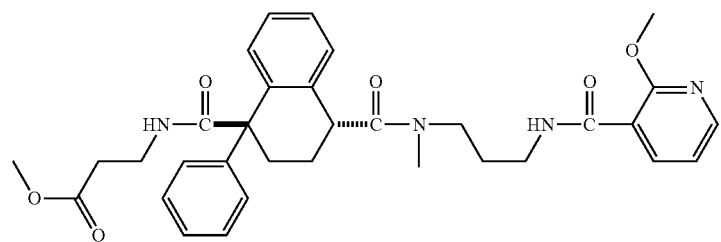
Co No. 32; Ex. B.6; trans
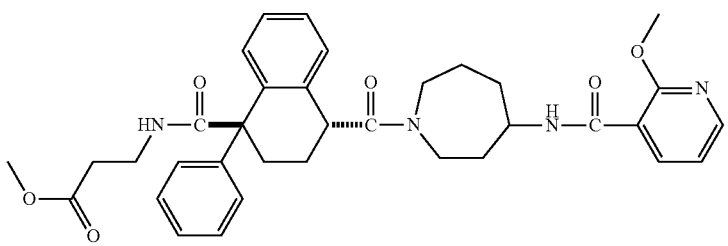
Co No. 33; Ex. B.6; trans
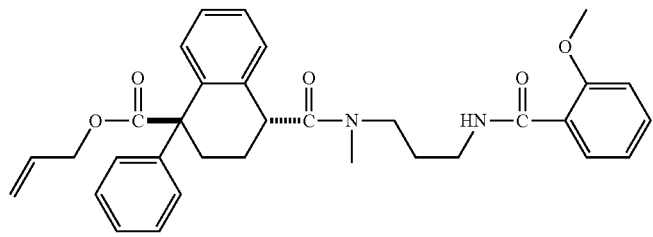
Co No. 34; Ex. B.4; trans
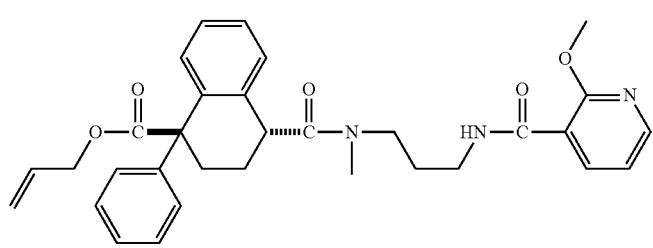
Co No. 35; Ex. B.4; trans
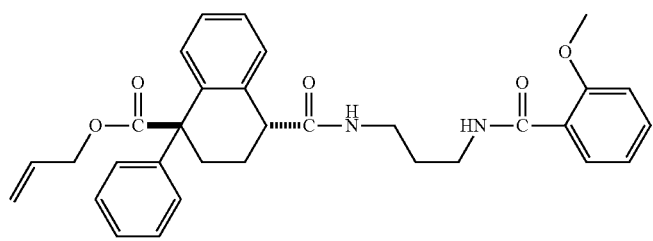
Co No. 36; Ex. B.4; trans
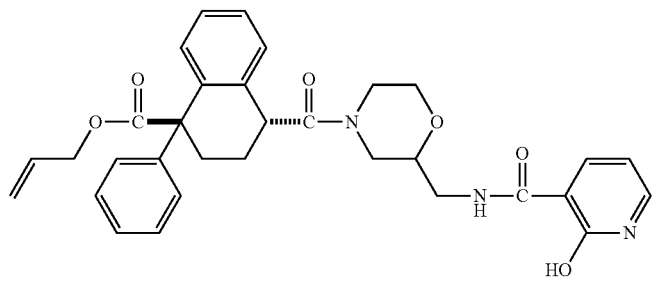
Co No. 37; Ex. B.4; trans TABLE F-1-continued
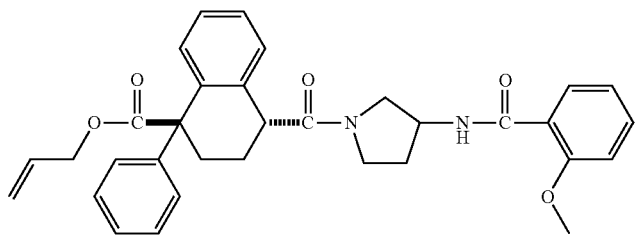
Co No. 38; Ex. B.4; trans
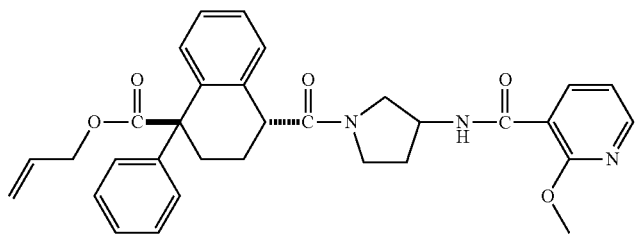
Co No. 39; Ex. B.4; trans
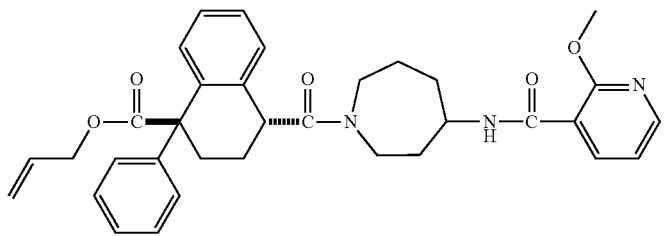
Co No. 40; Ex. B.4; trans
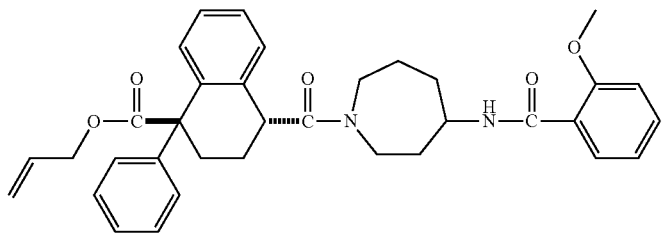
Co No. 41; Ex. B.4; trans
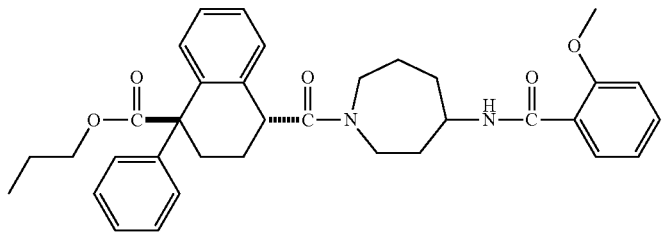
Co No. 42; Ex. B.5; trans
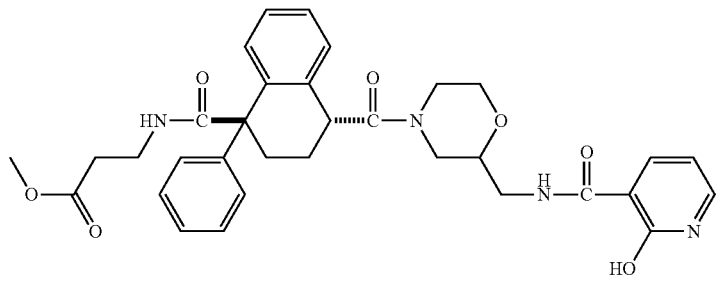
Co No. 43; Ex. B.6; trans

TABLE F-1-continued

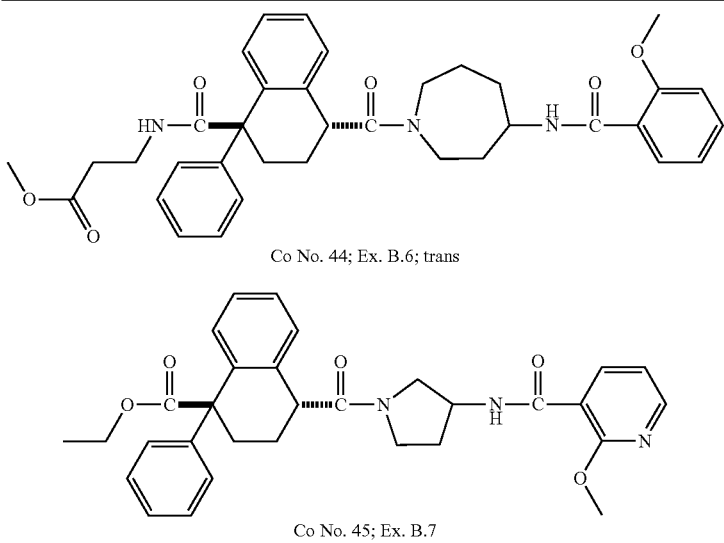

Co No. 44; Ex. B.6; trans

Co No. 45; Ex. B.7

Compound Identification

General Procedure A

The HPLC measurement was performed using an Alliance IIT 2790 (Waters) system comprising a quaternary pulp with degasser, an autosampler, a column oven (set at 40° C., unless otherwise indicated), a diode-array detector (DAD) and a column as specified in the respective methods below. Flow from the column was split to a MS spectrometer. The MS detector was configured with an electrospray ionization source. Mass spectra were acquired by scanning from 100 to 1000 in 1 second using a dwell time of 0.1 second. The capillary needle voltage was 3 kV and the source temperature was maintained at 140° C. Nitrogen was used as the nebulizer gas. Data acquisition was performed with a Waters-Micromass MassLynx-Openlynx data system.

General Procedure B

The LC measurement was performed using an Acquity HPLC (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Nitrogen was used as the nebulizer gas. Data acquisition was performed with a Waters-Micromass MassLynx-Openlynx data system.

Method 1 In addition to general procedure A: Reversed phase HPLC was carried out on an Xterra MS C18 column (3.5 µm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 1% A, 49% B and 50% C in 6.5 minutes, to 1% A and 99% B in 1 minute and hold these conditions for 1 minute and reequilibrate with 100% A for 1.5 minutes. An injection volume of 10 µl was used. Cone voltage was 10 V for positive ionization mode and 20 V for negative ionization mode.

Method 2

In addition to general procedure B: Reversed phase UPLC (Ultra Performance Liquid Chromatography) was carried out on a bridged ethylsiloxane/silica hybrid (BEH) C18 column (1.7 µm, 2.1×50 mm; Waters Acquity) with a flow rate of 0.8 ml/min. Two mobile phases (mobile phase A: 0.1% formic acid in $H_2O$/methanol 95/5; mobile phase B: methanol) were used to run a gradient condition from 95% A and 5% B to 5% A and 95% B in 1.3 minutes and hold for 0.2 minutes. An injection volume of 0.5 µl was used. Cone voltage was 10 V for positive ionization mode and 20 V for negative ionization mode.

Method 3

In addition to general procedure A: Reversed phase HPLC was carried out on a Chromolith (4.6×25 mm) with a flow rate of 3 ml/min. Three mobile phases (mobile phase A: 95% 25 mM ammoniumacetate+5% acetonitrile; mobile phase B: acetonitrile; mobile phase C: methanol) were employed to run a gradient condition from 96% A, 2% B and 2% C, to 49% B and 49% C in 0.9 minutes, to 100% B in 0.3 minutes and hold for 0.2 minutes. An injection volume of 2 PI was used. Cone voltage was 10 V for positive ionization mode and 20 V for negative ionization mode.

TABLE

Analytical data
When a compound is a mixture of isomers which give different peaks in the LCMS method, only the retention time of the main component is given in the LCMS table (Rt: Retention time in minutes).

| Co. No. | $R_t$ | $(MH)^+$ | Proc. |
|---|---|---|---|
| 1 | 5.93 | 471 | 1 |
| 2 | 6.06 | 501 | 1 |
| 3 | 6.65 | 615 | 1 |
| 4 | 6.06 | 485 | 1 |
| 5 | 6.19 | 515 | 1 |
| 6 | 6.72 | 629 | 1 |
| 7 | 6.05 | 485 | 1 |
| 8 | 6.16 | 515 | 1 |
| 9 | 6.76 | 629 | 1 |
| 10 | 6.19 | 499 | 1 |
| 11 | 6.32 | 529 | 1 |
| 12 | 6.79 | 643 | 1 |
| 13 | 6.06 | 471 | 1 |

TABLE-continued

Analytical data
When a compound is a mixture of isomers which give different peaks in the LCMS method, only the retention time of the main component is given in the LCMS table (Rt: Retention time in minutes).

| Co. No. | $R_t$ | $(MH)^+$ | Proc. |
|---|---|---|---|
| 14 | 6.16 | 501 | 1 |
| 15 | 6.72 | 615 | 1 |
| 16 | 6.13 | 485 | 1 |
| 17 | 6.23 | 515 | 1 |
| 18 | 6.76 | 629 | 1 |
| 19 | 6.15 | 485 | 1 |
| 20 | 6.16 | 515 | 1 |
| 21 | 6.79 | 629 | 1 |
| 22 | 6.22 | 499 | 1 |
| 23 | 6.32 | 529 | 1 |
| 24 | 6.82 | 643 | 1 |
| 25 | 5.68 | 515 | 1 |
| 26 | 5.68 | 515 | 1 |
| 27 | 5.81 | 529 | 1 |
| 28 | 5.82 | 529 | 1 |
| 29 | 1.34 | 541 | 2 |
| 30 | 1.36 | 542 | 2 |
| 31 | 1.20 | 586 | 2 |
| 32 | 1.18 | 587 | 2 |
| 33 | 1.19 | 613 | 2 |
| 36 | 1.08 | 527 | 3 |
| 37 | 5.61 | 556 | 1 |
| 38 | 6.20 | 539 | 1 |
| 39 | 6.14 | 540 | 1 |
| 40 | 6.40 | 568 | 1 |
| 41 | 6.42 | 567 | 1 |
| 42 | 1.43 | 569 | 2 |
| 43 | 1.03 | 601 | 2 |
| 44 | 1.20 | 612 | 2 |

Optical Rotation:

The optical rotation was measured using a polarimeter. $[\alpha]_D^{20}$ indicates the optical rotation measured with light at the wavelength of the D-line of sodium (589 nm) at a temperature of 20° C. Behind the actual value the concentration and solvent of the solution which was used to measure the optical rotation are mentioned.

| | Co. No. | $[\alpha]_D^{20}$ | concentration | solvent |
|---|---|---|---|---|
| 26117416 | 25 | −29.88° | 24.26 mg/5 ml | ethanol |
| 26117442 | 26 | +28.37° | 25.38 mg/5 ml | ethanol |
| 26117481 | 27 | +32.95° | 24.43 mg/5 ml | ethanol |
| 26117494 | 28 | −31.93° | 25.21 mg/5 ml | ethanol |

C. Pharmacological Examples

C.1. Quantification of the Secretion of ApoB

HepG2 cells were cultured in 24-well plates in MEM Rega 3 containing 10% fetal calf serum. At 70% confluency, the medium was changed and the test compound or carrier (DMSO, 0.4% final concentration) was added. After 24 hours of incubation, the medium was transferred to Eppendorf tubes and cleared by centrifugation. A sheep antibody directed against either apoB was added to the supernatant and the mixture was kept at 8° C. for 24 hours. Then, rabbit anti-sheep antibody was added and the immune complex was allowed to precipitate for 24 hours at 8° C. The immunoprecipitate was pelleted by centrifugation for 25 minutes at 1320 g and washed twice with a buffer containing 40 mM Mops, 40 mM $NaH_2PO_4$, 100 mM NaF, 0.2 mM DTT, 5 mM EDTA, 5 mM EGTA, 1% Triton-X-100, 0.5% sodium deoxycholate (DOC), 0.1% SDS, 0.2 mM leupeptin and 0.2 mM PMSF. Radioactivity in the pellet was quantified by liquid scintillation counting. The $IC_{50}$ values are usually converted to pIC50 values (=−log $IC_{50}$ value) for ease of use and summarized in Table C-1.

TABLE C-1 pIC50 values

| Co. No. | pIC50 |
|---|---|
| 4 | 6.499 |
| 5 | 6.716 |
| 6 | 7.37 |
| 7 | <6 |
| 8 | <6 |
| 9 | 6.893 |
| 10 | 6.127 |
| 11 | 6.177 |
| 12 | 7.634 |
| 16 | 6.102 |
| 17 | 6.382 |
| 18 | 6.51 |
| 19 | 6.642 |
| 20 | <6 |
| 21 | 6.62 |
| 22 | 6.179 |
| 23 | 6.224 |
| 24 | 7.635 |
| 25 | 7.761 |
| 26 | 6.252 |
| 28 | 7.018 |
| 29 | 6.985 |
| 30 | 7.115 |
| 31 | <6 |
| 32 | <6 |
| 33 | <6 |
| 42 | 6.544 |

C.2. MTP Assay

MTP activity was measured using an assay similar to one described by J. R. Wetterau and D. B. Zilversmit in *Chemistry and Physics of Lipids*, 38, 205-222 (1985). To prepare the donor and acceptor vesicles, the appropriate lipids in chloroform were put into a glass test tube and dried under a stream of $N_2$. A buffer containing 15 mM Tris-HCl pH 7.5, 1 mM EDTA, 40 mM NaCl, 0.02% $NaN_3$ (assay buffer) was added to the dried lipid. The mixture was vortexed briefly and the lipids were then allowed to hydrate for 20 min on ice. Vesicles were then prepared by bath sonication (Branson 2200) at room temperature for maximum 15 min. Butylated hydroxytoluene was included in all vesicle preparations at a concentration of 0.1%. The lipid transfer assay mixture contained donor vesicles (40 nmol phosphatidylcholine, 7.5 mol % of cardiolipin and 0.25 mol % glycerol tri[1-$^{14}$C]-oleate), acceptor vesicles (240 nmol phosphatidylcholine) and 5 mg BSA in a total volume of 675 μl in a 1.5 ml microcentrifuge tube. Test compounds were added dissolved in DMSO (0.13% final concentration). After 5 minutes of pre-incubation at 37° C., the reaction was started by the addition of MTP in 100 μl dialysis buffer. The reaction was stopped by the addition of 400 μl DEAE-52 cellulose pre-equilibrated in 15 mM Tris-HCl pH 7.5, 1 mM EDTA, 0.02% $NaN_3$ (1:1, vol/vol). The mixture was agitated for 4 min and centrifuged for 2 min at maximum speed in an Eppendorf centrifuge (4° C.) to pellet the DEAE-52-bound donor vesicles. An aliquot of the supernatant containing the acceptor liposomes was counted and the [$^{14}$C]-counts were used to calculate the percent triglyceride transfer from donor to acceptor vesicles.

TABLE C-2

| Co. No. | pIC50 |
|---|---|
| 1 | 5.902 |
| 2 | 6.391 |
| 3 | 6.681 |
| 4 | 7.654 |
| 5 | 8.028 |
| 6 | 8.018 |
| 7 | 7.068 |
| 8 | 7.568 |
| 9 | 7.718 |
| 10 | 8 |
| 11 | 8.245 |
| 12 | 8.198 |
| 13 | 5.269 |
| 14 | 5.604 |
| 15 | 5.56 |
| 16 | <7 |
| 17 | 7.428 |
| 18 | 7.209 |
| 19 | 6.883 |
| 20 | 7.151 |
| 21 | 7.317 |
| 22 | 7.785 |
| 23 | 7.935 |
| 24 | 8.214 |
| 25 | 8.186 |
| 26 | 6.761 |
| 27 | 6.112 |
| 28 | 8.144 |
| 29 | 7.398 |
| 30 | 7.633 |
| 31 | 7.186 |
| 32 | 6.78 |
| 33 | 7.097 |
| 42 | 7.639 |
| 43 | <6 |
| 44 | 7.277 |

The invention claimed is:

1. Compound of formula (I)

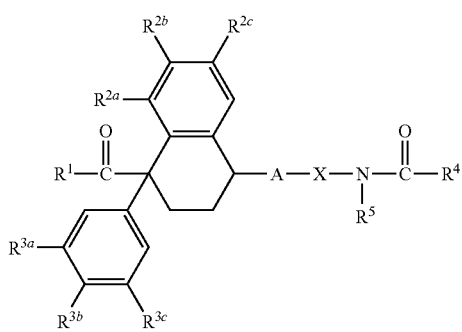

the pharmaceutically acceptable acid addition salts thereof, the N-oxides thereof, and the stereochemically isomeric forms thereof, wherein A is —(C=O)—;
X represents

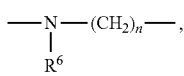

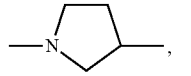

n is an integer 2 or 3;
$R^5$ is hydrogen or $C_{1-4}$alkyl;
$R^6$ is hydrogen or $C_{1-4}$alkyl;
$R^1$ is $NR^7R^8$, or $OR^9$;
wherein each $R^7$ and $R^8$ are independently selected from hydrogen, or
$C_{1-8}$alkyl substituted with $C_{1-4}$alkyloxycarbonyl
$R^9$ is $C_{1-8}$alkyl, or
$C_{3-8}$alkenyl;
$R^{2a}$, $R^{2b}$, and $R^{2c}$ are each hydrogen;
$R^{3a}$, $R^{3b}$, and $R^{3c}$ are each hydrogen;
$R^4$ is phenyl; phenyl substituted with $C_{1-4}$alkyloxy, or phenyl substituted with trifluoromethyl;
or pyridinyl substituted with hydroxy, or $C_{1-4}$alkyloxy.

2. Compound as claimed in claim 1 wherein $R^1$ is $NR^7R^8$.

3. Compound as claimed in claim 1 wherein $R^1$ is $OR^9$.

4. Compound as claimed in claim 1 wherein A represents —(C=O)—; $R^1$ is $OR^9$ wherein $R^9$ is $C_{1-6}$alkyl or $C_{3-8}$alkenyl; $R^{2a}$, $R^{3a}$, $R^{2b}$, $R^{3b}$, $R^{2c}$, and $R^{3c}$ are hydrogen; $R^4$ represents phenyl, phenyl substituted with $C_{1-4}$alkyloxy, pyridinyl substituted with hydroxy, or pyridinyl substituted with $C_{1-4}$alkyloxy; and X represents radical (a-1) wherein $R^5$ is hydrogen and $R^6$ is hydrogen or $C_{1-4}$alkyl.

5. A pharmaceutical composition comprising a pharmaceutically acceptable carrier and a therapeutically active amount of a compound as claimed in claim 1.

6. A process for preparing a pharmaceutical composition as claimed in claim 5 wherein the therapeutically active amount of the compound is intimately mixed with a pharmaceutically acceptable carrier.

7. A compound of formula (II)

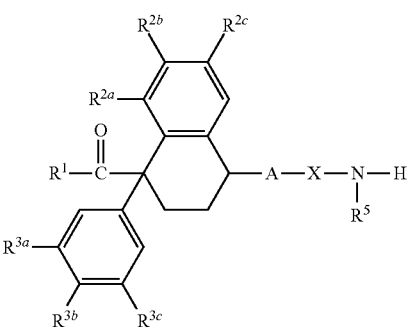

the pharmaceutically acceptable acid addition salts thereof, the N-oxides thereof, and the stereochemically isomeric forms thereof, wherein A is —(C=O)—;

X represents $$-\text{N}(\text{R}^6)-(\text{CH}_2)_n-,\quad \text{(a-1)}$$

[pyrrolidine structure] (a-2)

[azepane structure] (a-5)

n is an integer 2 or 3;
R$^5$ is hydrogen or C$_{1-4}$alkyl;
R$^6$ is hydrogen or C$_{1-4}$alkyl;
R$^1$ is NR$^7$R$^8$, or OR$^9$;
wherein each R$^7$ and R$^8$ are independently selected from hydrogen, or
C$_{1-8}$alkyl substituted with C$_{1-4}$alkyloxycarbonyl
R$^9$ is C$_{1-8}$alkyl, or
C$_{3-8}$alkenyl;
R$^{2a}$, R$^{2b}$, and R$^{2c}$ are each hydrogen;
R$^{3a}$, R$^{3b}$, and R$^{3c}$ are each hydrogen.

8. A compound of formula (XVII)

[structure of formula (XVII)]

the pharmaceutically acceptable acid addition salts thereof, the N-oxides thereof, and the stereochemically isomeric forms thereof, wherein
A is —(C=O)—;
X represents $$-\text{N}(\text{R}^6)-(\text{CH}_2)_n-,\quad \text{(a-1)}$$

[pyrrolidine structure] (a-2)

[azepane structure] (a-5)

n is an integer 2 or 3;
R$^5$ is hydrogen or C$_{1-4}$alkyl;
R$^6$ is hydrogen or C$_{1-4}$alkyl;
R$^{2a}$, R$^{2b}$, and R$^{2c}$ are each hydrogen;
R$^{3a}$, R$^{3b}$, and R$^{3c}$ are each hydrogen;
R$^4$ is phenyl; phenyl substituted with C$_{1-4}$alkyloxy, or phenyl substituted with trifluoromethyl;
or pyridinyl substituted with hydroxy, or C$_{1-4}$alkyloxy.

9. A process for preparing a compound of claim 1 wherein
a) an intermediate of formula (II) is reacted with an intermediate of formula (III) in a reaction-inert solvent and optionally in the presence of a suitable coupling reagent and/or a suitable base

[structure of formula (II)] +

[structure HO—C(=O)—R$^4$] (III) → (I)

b) or, a compound of formula (I) is converted into a pharmaceutically acceptable acid addition salt, or conversely, an acid addition salt of a compound of formula (I) is converted into a free base form with alkali; and, optionally preparing stereochemically isomeric forms thereof.

10. A process for preparing a compound of formula (I-a), defined as a compound of formula (I) of claim 1 wherein radical A represents —(C=O)—,
a) wherein an intermediate of formula (V) is reacted with an intermediate of formula (IV), in a reaction-inert solvent and optionally in the presence of a suitable coupling reagent and/or a suitable base

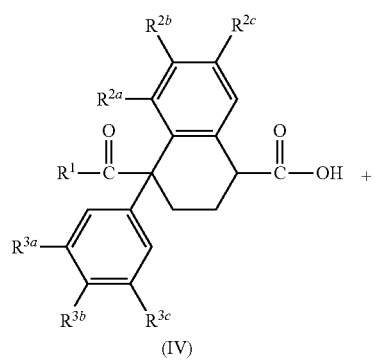
(IV)
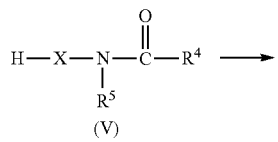
(V)
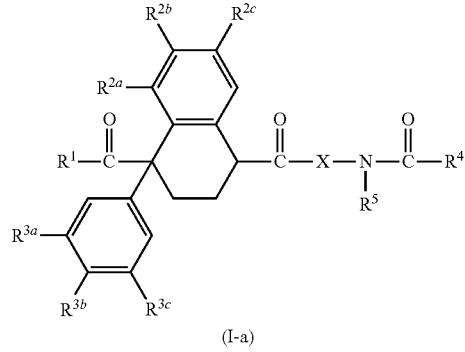
(I-a)
b) or, a compound of formula (I-a) is converted into a pharmaceutically acceptable acid addition salt, or conversely, an acid addition salt of a compound of formula (I-a) is converted into a free base form with alkali; and, optionally preparing stereochemically isomeric forms thereof.
* * * * *